(12) United States Patent
Tsai et al.

(10) Patent No.: US 9,206,246 B2
(45) Date of Patent: Dec. 8, 2015

(54) HEPARIN/HEPARAN SULFATE-DEPENDENT INHIBITORS OF ACTIVATED PROTEIN C AND USES THEREOF IN TREATING HEMOPHILIC DISORDERS

(71) Applicant: Academia Sinica, Taipei (TW)

(72) Inventors: Inn-Ho Tsai, Taipei (TW); An-Chun Cheng, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/081,427

(22) Filed: Nov. 15, 2013

(65) Prior Publication Data

US 2014/0142040 A1   May 22, 2014

Related U.S. Application Data

(60) Provisional application No. 61/727,530, filed on Nov. 16, 2012.

(51) Int. Cl.
   *A61K 38/00*  (2006.01)
   *C07K 14/00*  (2006.01)
   *C07K 14/81*  (2006.01)
   *C07K 14/46*  (2006.01)

(52) U.S. Cl.
   CPC ........... *C07K 14/8114* (2013.01); *C07K 14/463* (2013.01); *A61K 38/00* (2013.01)

(58) Field of Classification Search
   CPC ... A61K 38/00; C07K 14/463; C07K 14/8114
   USPC .......................................... 514/14.2; 530/324
   See application file for complete search history.

(56) References Cited

U.S. PATENT DOCUMENTS

| | | | |
|---|---|---|---|
| 5,786,328 A | * | 7/1998 | Dennis et al. ................. 514/20.1 |
| 2006/0013812 A1 | | 1/2006 | Rojkjaer |

OTHER PUBLICATIONS

Kim et al, "Low prevalence of activated protein C resistance and coagulation factor V Arg506 to Gln mutation among Korean patients with deep vein thrombosis," J. Korean Med. Sci., 1998, 13: 587-590.*

Rudinger J, "Characteristics of the amino acids as components of a peptide hormone sequence," Peptide Hormones, JA Parsons Edition, University Park Press, Jun. 1976, pp. 1-7.*

"Designing Custom Peptides," from SIGMA Genosys, pp. 1-2. Accessed Dec. 16, 2004.*

Schinzel R, Drueckes P, "The phosphate recognition site of Escherichia coli maltodextrin phosphorylase," FEBS, Jul. 1991, 286(1,2): 125-128.*

Berendsen HJC, "A Glimpse of the Holy Grail?" Science, 1998, 282: 642-643.*

Voet D, Voet JG, Biochemistry, Second Edition, John Wiley & Sons, Inc., 1995, pp. 235-241.*

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*

Cheng et al., A novel heparin-dependent inhibitor of activated protein C that potentiates consumptive coagulopathy in Russell's viper envenomation. J Biol Chem. May 4, 2012 ;287(19):15739-48; doi:10.1074/jbc.M111.323063. Epub Mar 13, 2012.

GenBank; NIH/NCBI, Accession No. A8Y7N4.1, Guo et al., Jun. 16, 2009, 2 pages.

GenBank; NIH/NCBI, Accession No. AFB74192.1, Cheng et al., May 8, 2012, 1 page.

* cited by examiner

*Primary Examiner* — Julie Ha

(74) *Attorney, Agent, or Firm* — Wolf, Greenfield & Sacks, P.C.

(57) ABSTRACT

Methods for inhibiting activated protein C (APC) comprising contacting the APC with a Kunitz polypeptide in an amount effective in inhibiting the activity of APC, wherein the Kunitz polypeptide comprises six cysteine residues at positions corresponding to positions 7, 16, 32, 40, 53, and 57 in SEQ ID NO:1, a motif $X_1GX_2CBX'$ at positions corresponding to positions 13-18 in SEQ ID NO:1, wherein each of $X_1$ and $X_2$, independently, is any amino acid residue, B is a basic amino acid residue, and X' is G, A, or V; and at least one heparin-binding motif, which can present at the C-terminus of the Kunitz polypeptide.

8 Claims, 9 Drawing Sheets

SEQUENCE LISTING

```
<160> NUMBER OF SEQ ID NOS: 13

<210> SEQ ID NO 1
<211> LENGTH: 66
<212> TYPE: PRT
<213> ORGANISM: Artificial Sequence
<220> FEATURE:
<223> OTHER INFORMATION: Synthetic Polypeptide

<400> SEQUENCE: 1

Gln Asp Arg Pro Lys Phe Cys Asn Leu Ala Pro Glu Ser Gly Arg Cys
1               5                   10                  15

Arg Gly His Leu Arg Arg Ile Tyr Tyr Asn Pro Asp Ser Asn Lys Cys
            20                  25                  30

Glu Val Phe Phe Tyr Gly Gly Cys Gly Gly Asn Asp Asn Asn Phe Glu
        35                  40                  45

Thr Arg Lys Lys Cys Arg Gln Thr Cys Gly Ala Pro Arg Lys Gly Arg
    50                  55                  60

Pro Thr
65

<210> SEQ ID NO 2
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 2

His Asp Arg Pro Thr Phe Cys Asn Leu Ala Pro Glu Ser Gly Arg Cys
1               5                   10                  15

Arg Ala His Leu Arg Arg Ile Tyr Tyr Asn Leu Glu Ser Asn Lys Cys
            20                  25                  30
```

```
Glu Val Phe Phe Tyr Gly Gly Cys Gly Gly Asn Asp Asn Asn Phe Ser
            35                  40                  45

Thr Trp Asp Glu Cys Arg His Thr Cys Val Gly Lys
 50                  55                  60

<210> SEQ ID NO 3
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 3

Cys Gly Gly Asn Asp Asn Asn Phe Glu Thr Arg Lys Lys Cys Arg Gln
 1               5                  10                  15

Thr Cys Gly Ala Pro Arg Lys Gly Arg Pro Thr
            20                  25

<210> SEQ ID NO 4
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 4

Cys Gly Gly Asn Asp Asn Asn Phe Glu Thr Ala Ala Ala Cys Arg Gln
 1               5                  10                  15

Thr Cys Gly Ala Pro Arg Lys Gly Arg Pro Thr
            20                  25

<210> SEQ ID NO 5
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 5

Cys Gly Gly Asn Asp Asn Asn Phe Glu Thr Arg Lys Lys Cys Arg Gln
 1               5                  10                  15

Thr Cys Gly Ala
            20

<210> SEQ ID NO 6
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 6

Cys Gly Gly Asn Asp Asn Asn Phe Glu Thr Ala Ala Ala Cys Arg Gln
 1               5                  10                  15

Thr Cys Gly Ala Pro Ala Ala Gly Ala Pro Thr
            20                  25

<210> SEQ ID NO 7
<211> LENGTH: 17
<212> TYPE: PRT
<213> ORGANISM: Artificial Sequence
<220> FEATURE:
<223> OTHER INFORMATION: Synthetic Polypeptide
```

```
<400> SEQUENCE: 7

Thr Arg Lys Lys Cys Arg Gln Thr Cys Gly Ala Pro Arg Lys Gly Arg
1               5                   10                  15

Pro

<210> SEQ ID NO 8
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 8

Thr Arg Lys Lys Cys Arg Gln
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 9

Pro Arg Lys Gly Arg Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

Ser Gly Arg Cys Arg Gly
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(2)
<223> OTHER INFORMATION: Xaa represents a basic amino acid
<220> FEATURE:
<221> NAME/KEY: MISC_FEATURE
<222> LOCATION: (4)..(4)
<223> OTHER INFORMATION: Xaa represents a basic amino acid
<220> FEATURE:
<221> NAME/KEY: MISC_FEATURE
<222> LOCATION: (5)..(6)
<223> OTHER INFORMATION: Xaa represents a non-charged amino acid
<220> FEATURE:
<221> NAME/KEY: MISC_FEATURE
<222> LOCATION: (8)..(9)
<223> OTHER INFORMATION: Xaa represents a non-charged amino acid
<220> FEATURE:
<221> NAME/KEY: MISC_FEATURE
<222> LOCATION: (11)..(12)
<223> OTHER INFORMATION: Xaa represents a basic amino acid
<220> FEATURE:
<221> NAME/KEY: MISC_FEATURE
<222> LOCATION: (13)..(13)
<223> OTHER INFORMATION: Xaa represents a non-charged amino acid
```

-continued

```
<220> FEATURE:
<221> NAME/KEY: MISC_FEATURE
<222> LOCATION: (14)..(14)
<223> OTHER INFORMATION: Xaa represents a basic amino acid

<400> SEQUENCE: 11

Xaa Xaa Cys Xaa Xaa Xaa Cys Xaa Xaa Pro Xaa Xaa Xaa Xaa Pro
1               5                   10                  15

<210> SEQ ID NO 12
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 12
ccagacggct ccatcatg                                                18

<210> SEQ ID NO 13
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 13
aaaaggaatr atccagg                                                 17
```

HEPARIN/HEPARAN SULFATE-DEPENDENT INHIBITORS OF ACTIVATED PROTEIN C AND USES THEREOF IN TREATING HEMOPHILIC DISORDERS

RELATED APPLICATION

This application claims the benefit of U.S. provisional application No. 61/727,530, filed Nov. 16, 2012 under 35 U.S.C. §119, the entire content of which is herein incorporated by reference.

BACKGROUND OF THE INVENTION

Hemophilia A and B are bleeding disorders caused by deficiencies in coagulation factor VIII (FVIII) and IX (FIX), respectively. Affected individuals often suffer from spontaneous internal bleedings, the most severe of which could lead to intracranial hemorrhage and death [1]. Current treatments rely heavily on the administration of either plasma-derived or recombinant factor concentrates. However, their usage is limited due to the high cost of recombinant concentrates and the risks of viral transmissions associated with contaminated blood products. Furthermore, it has been estimated that 10-15% of hemophilia A patients and 1-3% of hemophilia B patients develop neutralizing antibodies that render factor replacements ineffective for these patients [2]. It is therefore of great importance to develop new approaches to meet the needs of hemophilia patients.

Several clinical studies have suggested that the severity of bleeding phenotypes in hemophilia patients can be moderated by a fairly common mutation in the factor V (FV) gene known as the factor V Leiden mutation (FVL) [3-7]. Patients carrying this mutation have activated cofactors FVa that are resistant to degradation by activated protein C (APC), a serine protease that normally degrades FVa and FVIIIa [8]. Hemophilia A and B mice carrying the same mutation showed improved hemostasis in vivo, particularly at the microcirculation level, suggesting that APC could be a new target for hemophilia treatment [9]. Over the past few years, several groups have shown that the inhibition of APC by chemically synthesized inhibitors leads to the prolongation of FVa function and is accompanied by increases in thrombin generation and clot weight in hemophilia A blood [10, 11]. These inhibitors, however, have high inhibition constants ($K_i$ values in the micromolar ranges) and are not fully selective against thrombin, which limit their therapeutic usage.

SUMMARY OF THE INVENTION

The present disclosure is based on the unexpected discoveries that a Kunitz peptide isolated from a RVV (e.g., SEQ ID NO:1) and variants thereof, which comprises a Kunitz domain and at least one heparin-binding motif, is effective in inhibiting the activity of activated protein C (APC). Such a Kunitz peptide is therefore useful in treating hemophilic disorders.

Accordingly, one aspect of the present disclosure relates to a method for inhibiting APC, comprising contacting the APC with a Kunitz polypeptide in an amount effective in inhibiting the activity of APC. The Kunitz polypeptide comprises: (a) six cysteine residues at positions corresponding to positions 7, 16, 32, 40, 53, and 57 in SEQ ID NO:1, (b) a motif $X_1GX_2CBX'$ at positions corresponding to positions 13-18 in SEQ ID NO:1, wherein each of $X_1$ and $X_2$, independently, is any amino acid residue, B is a basic amino acid residue, and X' is G, A, or V; and (c) at least one heparin-binding motif.

In some embodiments, $X_2$ in the motif of $X_1GX_2CBX'$ is R, V, or I. In other embodiments, $X_2$ in the motif of $X_1GX_2CBX'$ is R, B is R, and optionally, X' is A or G.

The at least one heparin-binding motif can be selected from the group consisting of:

$Z_1BZ_2$, in which each of $Z_1$ and $Z_2$, independently, is a non-charged amino acid residue, and B is a basic amino acid;

$Z_1B_1B_2Z_2$, in which each of $Z_1$ and $Z_2$, independently, is a non-charged amino acid residue, and each of $B_1$ and $B_2$, independently, is a basic amino acid;

$Z_1B_1B_2B_3Z_2$, in which each of $Z_1$ and $Z_2$, independently, is a non-charged amino acid residue, and each of $B_1$-$B_3$, independently, is a basic amino acid, $Z_1B_1B_2B_3B_4Z_2$, in which each of $Z_1$ and $Z_2$, independently, is a non-charged amino acid residue, and each of $B_1$-$B_4$, independently, is a basic amino acid, and a combination thereof.

In some examples, the at least one heparin-binding motif is:

$Z_1B_1B_2B_3Z_2B_4Z_3$, in which each of $Z_1$-$Z_3$, independently, is a non-charged amino acid residue and each of B1-B4, independently, is a basic amino acid residue, or $Z_1B_1B_2Z_2B_3Z_3$, in which each of $Z_1$-$Z_3$, independently, is a non-charged amino acid residue and each of B1-B3, independently, is a basic amino acid residue.

In some embodiments, the Kunitz polypeptide described herein comprises at its C-terminus a heparin-binding domain set forth as $B_1B_2CB_3Z_1Z_2CZ_3Z_4PB_4B_5Z_5B_6P$ (SEQ ID NO:11), in which each of $Z_1$-$Z_5$, independently, is a non-charged amino acid residues, and each of $B_1$-$B_6$, independently, is a basic amino acid residue.

In other embodiments, the present disclosure relates to a method for inhibiting activated protein C (APC), comprising contacting the APC with a Kunitz polypeptide in an amount effective in inhibiting the activity of APC, wherein the Kunitz polypeptide comprises an amino acid sequence at least 85% (e.g., 90%, 95%, 97%, 98%, or 99%) identical to SEQ ID NO:1.

In any of the methods described above, the contacting step can be performed by administering to a subject in need thereof the Kunitz polypeptide. In one example, the subject is administered with the Kunitz polypeptide in an amount effective in promoting blood coagulation.

The subject to be treated by the methods described herein can be a human patient suffering from or suspected of having a hemophilic disorder.

In another aspect, the present disclosure relates to a method for treating a hemophilia disorder, comprising administering to a subject in need thereof an effective amount of any of the Kunitz polypeptide as described herein.

Also within the scope of the present disclosure are (i) a pharmaceutical composition for use in treating a hemophilia disorder, the pharmaceutical composition comprising any of the Kunitz polypeptides described herein and a pharmaceutically acceptable carrier, and (ii) use of the just-described pharmaceutical composition in manufacturing a medicament for use in the treatment of a hemophilia disorder.

Further, the present disclosure features an isolated polypeptide comprising the amino acid sequence of SEQ ID NO:1 or a variant thereof that comprises one of the heparin-binding motifs in SEQ ID NO:1, a pharmaceutical composition comprising the polypeptide and a pharmaceutically acceptable carrier, an isolated nucleic acid, comprising a nucleotide sequence encoding a polypeptide comprising the amino acid sequence of SEQ ID NO:1, a vector (e.g., an expression vector) comprising the nucleic acid described herein, and an isolated host cell comprising the just-noted vector.

An "isolated polypeptide," "isolated nucleic acid," or "isolated cell," a used herein, refers to a polypeptide, a nucleic acid, or a cell substantially free from naturally associated molecules, i.e., the naturally associated molecules constituting at most 20% by dry weight of a preparation containing the polypeptide, nucleic acid, or cell. Purity can be measured by any appropriate method, e.g., column chromatography, polyacrylamide gel electrophoresis, and HPLC.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

Figure 1:
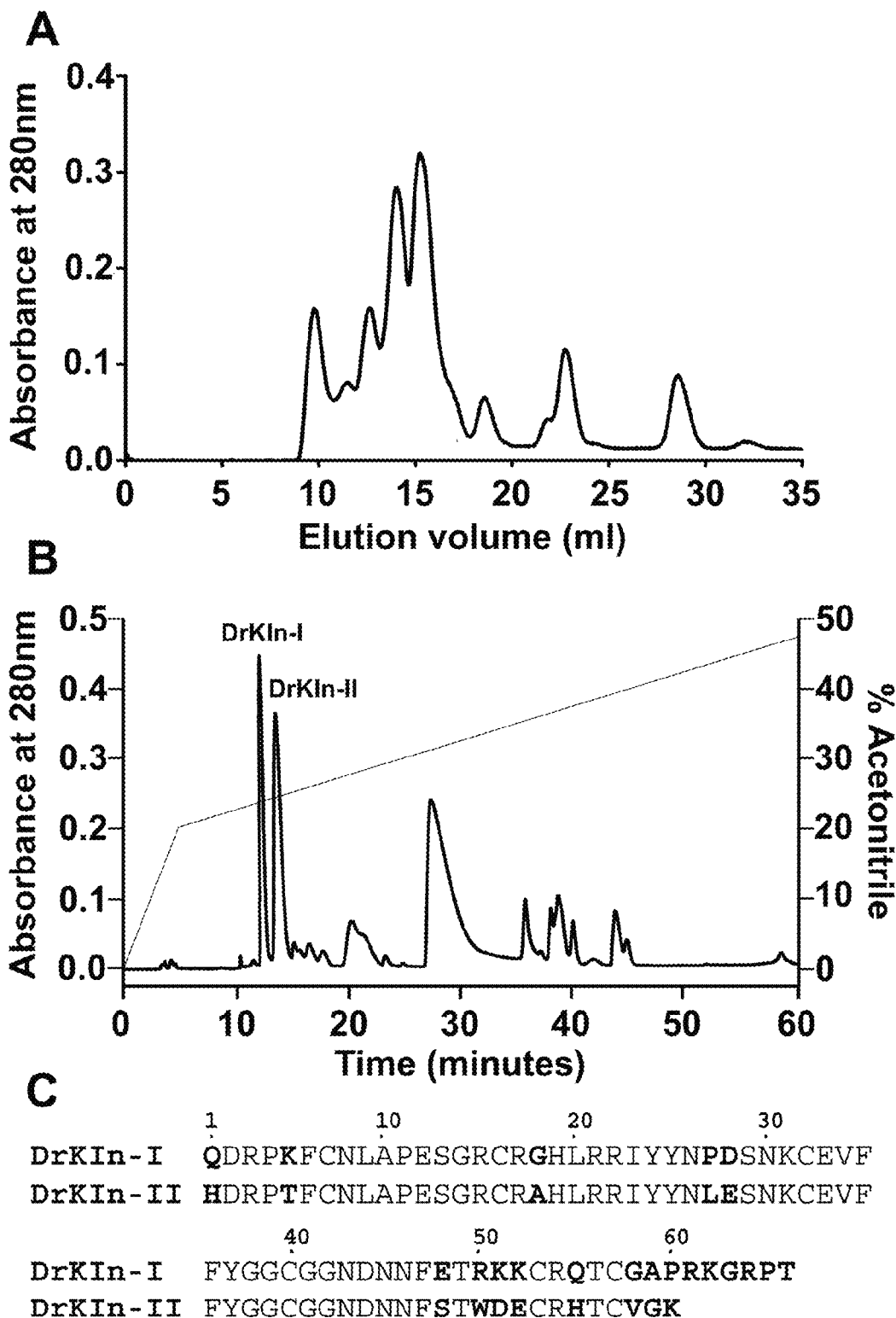
FIG. 1 shows purification of Kunitz-type protease inhibitors. A, 20 mg of *Daboia russelii russelii* crude venom was dissolved in 0.1 M ammonium acetate buffer (pH 6.5) and fractionated by gel filtration using FPLC. The fractions containing Kunitz-type protease inhibitors (indicated by a horizontal bar) were pooled together and lyophilized. B, Subsequent fractionation using reversed-phase HPLC. A linear gradient of 20-50% acetonitrile was applied over a period of 60 minutes. The protein peaks corresponding to DrKIn-I and DrKIn-II were indicated. C, Amino acid sequences of DrKIn-I (SEQ ID NO:1) and DrKIn-II (SEQ ID NO:2). Non-identical amino acids are denoted in bold letters.

Hemophilia A and B are bleeding disorders caused by deficiencies in coagulation factor VIII (FVIII) and IX (FIX), respectively. Affected individuals often suffer from spontaneous internal bleedings, the most severe of which could lead to intracranial hemorrhage and death.

The present disclosure is based on the identification of a Kunitz-type protease inhibitor named DrKIn-I (*Daboia russelii* Kunitz Inhibitor-I) from Russell's viper venom, which exhibits unexpectedly high specificity and potency against APC in the presence of heparan sulfate or heparin [12]. This 66 amino acid polypeptide inhibited APC with a $K_i$ value of approximately 50 pM and showed no inhibitory activities against thrombin and factor Xa (FXa). The isolation and kinetic characterization of this novel APC inhibitor are described herein and the results demonstrated that DrKIn-I binds tightly to APC, both in purified system and in plasma. Moreover, the therapeutic potential of DrKIn-I and its variants as described herein was evaluated and the results showed that this inhibitor could significantly neutralize the effect of APC and improve tissue factor (TF)-initiated thrombin generation in FVIII and FIX-deficient plasma. In sum, the evidence provided in the present disclosure demonstrate that DrKIn-I and it's functional variants as those described herein as novel APC inhibitors, can compensate for factor deficiencies in hemophilic patients and thus be effective in treating hemophilic disorders such as Hemophilia A and B.

Accordingly, the present disclosure is based on the unexpected discovery of a potent Kunitz-type APC inhibitor, DrKIn-I. Using chromogenic substrate, DrKIn-I dose-dependently inhibited the activity of APC. Heparin potentiated the inhibition and reduced the IC50 of DrKIn-I by 25-fold. DrKIn-I, together with heparin, also protected factor Va from APC-mediated inactivation. Using surface plasmon resonance, DrKIn-I exhibited fast binding kinetics with APC (association rate constant=$1.7 \times 10^7$ $M^{-1}$ $s^{-1}$). Direct binding assays and kinetic studies revealed that this inhibition ($K_i$=53 pM) is due to the tight binding interactions of DrKIn-I with both heparin and APC. DrKIn-I also effectively reversed the anticoagulant activity of APC and completely restored the thrombin generation in APC-containing plasma. Furthermore, DrKIn-I was found to be able to compensate for the hemostatic defects in FVIII- or FIX-deficient plasma, as evidenced by both APTT-based clotting and thrombin generation assays. In the presence of DrKIn-I, the levels of thrombin generation triggered by TF in FVIII-deficient or FIX-deficient plasma approached, or in some cases exceeded, that in normal plasma. Finally, mutants of DrKIn-I that lack either of the two C-terminal heparin/heparan sulfate-binding motifs in DrKIn-I exhibited APC inhibitory activity in the presence of heparin but not heparan sulfate, and mutant of DrKIn-I that lack both of the C-terminal heparin-binding motifs had diminished APC inhibitory activity, indicating that presence of at least one C-terminal heparin/heparan sulfate-binding motif is important for APC inhibition.

Described herein are Kunitz polypeptides, such as DrKIn-I and its functional variants and uses thereof for inhibiting the activity of activated protein C (APC), promoting blood coagulation, and/or treating a hemophilia disorder using a Kunitz polypeptide.

I. Kunitz Polypeptides

The Kunitz polypeptides described herein each comprise a Kunitz domain and at least one heparin-binding motif (e.g., 2, 3, or more), which preferably is at the C-terminus of a Kunitz polypeptide. The term "polypeptide" used herein refers to a polymer composed of multiple amino acid monomers. Preferably, each of the Kunitz polypeptides described herein includes up to 200 (e.g., up to 150, 120, 100, or 80) amino acids. In some examples, the Kunitz polypeptides each contain about 60-80 amino acid residues (e.g., about 65-80, 65-75, or amino acid residues). These peptides can contain naturally-occurring amino acid residues, or modified amino acids. In one example, either the N-terminus or the C-terminus of a Kunitz polypeptide is modified, e.g., containing an $—NH_2$ group at the C-terminus. In some examples, the Kunitz polypeptide described herein is a cyclic molecule.

The Kunitz domain typically comprises at least two (e.g., 3, 4, 5, or 6) cysteine residues at positions corresponding to positions 7, 16, 32, 40, 53, and 57 in SEQ ID NO:1 (in bold-face) and a $X_1GX_2CBX'$ motif (underlined) at positions corresponding to positions 13-18 in SEQ ID NO:1, wherein each of $X_1$ and $X_2$, independently, is any amino acid residue (e.g., R, V, or I), B is a basic amino acid residue (e.g., R or K), and X' is preferably a small aliphatic amino acid residue, such as G, A, or V. In one example, $X_1GX_2CBX'$ motif is SGRCRG (SEQ ID NO:10).

(SEQ ID NO: 1)

QDRPKFCNLA PE<u>SGRCRG</u>HL RRIYYNPDSN KCEVFFYGGC

GGNDNNFEtr kkcrqTCGAp rkgrpT

The heparin-binding motif, which preferably is located at the C-terminus of a Kunitz polypeptide, can be $Z_1BZ_2$, in which each of $Z_1$ and $Z_2$ is a non-charged amino acid residue and B is a basic amino acid residue; $Z_1BZ_2$, in which each of $Z_1$ and $Z_2$, independently, is a non-charged amino acid residue, and B is a basic amino acid; $Z_1B_1B_2Z_2$, in which each of $X_1$ and $X_2$, independently, is a non-charged amino acid residue, and each of $B_1$ and $B_2$, independently, is a basic amino acid; $Z_1B_1B_2B_3Z_2$, in which each of $Z_1$ and $Z_2$, independently, is a non-charged amino acid residue, and each of $B_1$-$B_3$, independently, is a basic amino acid; or $Z_1B_1B_2B_3B_4Z_2$, in which each of $Z_1$ and $Z_2$, independently, is a non-charged amino acid residue, and each of $B_1$-$B_4$, independently, is a basic amino acid.

In some embodiments, the at least one heparin-binding motif in the Kunitz polypeptide is $Z_1B_1B_2B_3X_2B_4Z_3$, in which each of $Z_1$-$Z_3$, independently, is a non-charged amino acid residue as described herein and each of B1-B4, independently, is a basic amino acid residue (e.g., R or K), or $Z_1B_1B_2X_2B_3Z_3$, in which each of $Z_1$-$Z_3$, independently, is a non-charged amino acid residue and each of B1-B3, independently, is a basic amino acid residue.

The non-charged amino acid residues in any of the heparin-binding motifs noted above can be G, A, V, I, L, M, F, Y, W, C or P, and the basic amino acid residue can be R or K.

The Kunitz polypeptides described herein can include one of the heparin-binding motif described herein, or any combination thereof. In one example, the Kunitz polypeptide comprises at its C-terminus a heparin-binding domain set forth as $B_1B_2CB_3Z_1Z_2CZ_3Z_4PB_4B_5Z_5B_6P$ (SEQ ID NO:11), in which each of $Z_1$-$Z_5$, independently, is a non-charged amino acid residue, and each of $B_1$-$B_6$, independently, is a basic amino acid residue. In a preferred example, the heparin-binding domain is TRKKCRQTCGAPRKGRP (SEQ ID NO:7; corresponding to positions 49-65 in SEQ ID NO:1), which includes two heparin-binding motifs: $^{49}$TRKKCRQ$^{55}$ (SEQ ID NO:8) and $^{60}$PRKGRP$^{65}$ (SEQ ID NO:9). See lower case letters in SEQ ID NO:1.

Alternatively or in addition, the Kunitz polypeptide comprises an amino acid sequence at least 85% (e.g., 88%, 90%, 93%, 95%, 96%, 97%, 98%, or 99%) identical to SEQ ID NO:1. The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The skilled artisan will realize that conservative amino acid substitutions may be made in SEQ ID NO:1 to provide the Kunitz polypeptides described herein. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of SEQ ID NO:1 typically are made by alteration of a nucleic acid encoding the mutant. Such substitutions can be made by a variety of methods known to one of ordinary skill in the art. For example, amino acid substitutions may be made by PCR-directed mutation, site-directed mutagenesis according to the method of Kunkel (Kunkel, PNAS 82: 488-492, 1985), or by chemical synthesis of a nucleic acid molecule encoding a Kunitz polypeptide as described herein.

Any of the Kunitz polypeptides described herein can be prepared via conventional methods, e.g., chemical synthesis or recombinant technology. Nucleic acids encoding the Kunitz polypeptides described herein, vectors (e.g., expression vectors) comprising such nucleic acids, and host cells comprising the vectors are also within the scope of the present disclosure. In some embodiments, the Kunitz polypeptide can be fused with a heterologous sequence such as a protein tag (e.g., a His-tag or a SUMO tag).

II. Pharmaceutical Composition

One or more of the above-described Kunitz polypeptides can be mixed with a pharmaceutically acceptable carrier (excipient), including buffer, to form a pharmaceutical composition for use in alleviating a hemophilia disorder. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

In some embodiments, the pharmaceutical compositions described herein further comprise heparin or heparan sulfate (e.g., an oligosaccharide having three di-saccharide units).

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the Kunitz polypeptide, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., a Kunitz polypeptide) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the Kunitz polypeptide, in which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773, 919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a Kunitz polypeptide with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

III. Treatment Methods

To practice the method disclosed herein, an effective amount of any of the pharmaceutical compositions described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, Kunitz polypeptides can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a hemophilia disorder, which is a group of disorders (e.g., hereditary genetic disorders) that impair the body's ability to control blood clotting or coagulation for stopping bleeding when a blood vessel is broken. Hemophilic disorders include, but are not limited to, Haemophilia A (factor VIII deficiency), Haemophilia B (factor IX deficiency), and Haemophilia C (factor XI deficiency).

A subject having a hemophilic disorder can be identified by routine medical examination, e.g., laboratory tests or genetic tests. A subject suspected of having a hemophilic disorder might show one or more symptoms of the disorder, e.g., frequent external or internal bleeding and longer blood clotting time as compared to healthy subjects. A subject at risk for a hemophilic disorder can be a subject having one or more of the risk factors for that disorder, e.g., gender (occur more frequently in men than in women), and family history.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of the hemophilic disorder. Alternatively, sustained continuous release formulations of a Kunitz polypeptide may be appropriate. Various formulations and devices for achieving sustained release are known in the art.

In one example, dosages for a Kunitz polypeptide as described herein may be determined empirically in individuals who have been given one or more administration(s) of the Kunitz polypeptide. Individuals are given incremental dosages of the antagonist. To assess efficacy of the antagonist, an indicator of blood clotting ability can be followed.

Generally, for administration of any of the Kunitz polypeptide described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate the hemophilic disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, every 10 weeks; or once every month, every 2 months, or every 3 months, or longer. The progress of this therapy is easily monitored by conventional techniques and assays. The dosing regimen (including the antibody used) can vary over time.

A pharmaceutical composition comprising a Kunitz polypeptide as described herein may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a Kunitz polypeptide will depend on the specific Kunitz polypeptide (or compositions thereof) employed, the type and severity of the disorder, whether the Kunitz polypeptide is administered for preventive or therapeutic purposes, previous therapy, the patient's clinical history and response to the Kunitz polypeptide, and the discretion of the attending physician. Typically the clinician will administer a Kunitz polypeptide until a dosage is reached that achieves the desired result. Administration of a Kunitz polypeptide can be continuous or intermittent, depending, for example, upon the recipient's physiological condition, whether the purpose of the administration is therapeutic or prophylactic, and other factors known to skilled practitioners. The administration of a Kunitz polypeptide may be essentially continuous over a preselected period of time or may be in a series of spaced dose.

In some embodiments, one or more Kunitz polypeptides as described herein can be co-administered with a co-factor such as heparan sulfate (which can be an oligosaccharide having as less as three di-saccharide units), dermatan sulfate, chondroitin sulfate, Enoxaparin (short heparin chain) and DNA (either single stranded or double stranded). One or more such co-factors can be formulated together with the Kunitz polypeptide(s) or formulated separately.

As used herein, the term "treating" refers to the application or administration of a composition including one or more active agents to a subject, who has a hemophilic disorder, a symptom of the disorder, or a predisposition toward the disorder, with the purpose to cure, heal, alleviate, relieve, alter, remedy, ameliorate, improve, or affect the disorder, the symptom of the disorder, or the predisposition toward the disorder.

Alleviating a hemophilic disorder includes delaying the development or progression of the disorder, or reducing disease severity. Alleviating the disorder does not necessarily require curative results. As used therein, "delaying" the development of a disorder (such as a hemophilic disorder) means to defer, hinder, slow, retard, stabilize, and/or postpone progression of the disorder. This delay can be of varying lengths of time, depending on the history of the disorder and/or individuals being treated. A method that "delays" or alleviates the development of a disorder, or delays the onset of the disorder, is a method that reduces probability of developing one or more symptoms of the disorder in a given time frame and/or reduces extent of the symptoms in a given time frame, when compared to not using the method. Such comparisons are typically based on clinical studies, using a number of subjects sufficient to give a statistically significant result.

"Development" or "progression" of a disorder means initial manifestations and/or ensuing progression of the disorder. Development of the disorder can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

In some embodiments, the Kunitz polypeptide described herein is administered to a subject in need of the treatment at an amount sufficient to reduce the blood clotting time by at least 20% (e.g., 30%, 40%, 50%, 60%, 70%, 80%, 90% or greater). In other embodiments, conventional methods, known to those of ordinary skill in the art of medicine, can be used to administer the pharmaceutical composition to the subject, depending upon the type of disease to be treated. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble polypeptide can be administered by the drip method, whereby a pharmaceutical formulation containing the polypeptide and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

The therapeutic Kunitiz polypeptide or its encoding polynucleotides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

IV. Kits for Use in Treating Hemophilic Disorder

The present disclosure also provides kits for use in treating or alleviating a hemophilic disorder. Such kits can include one or more containers comprising a Kunitz polypeptide as described herein (e.g., SEQ ID NO:1 or a functional variant thereof).

In some embodiments, the kit can comprise instructions for use in accordance with any of the methods described herein. The included instructions can comprise a description of administration of the Kunitz polypeptide to treat, delay the onset, or alleviate a hemophilia disorder according to any of the methods described herein. The kit may further comprise a description of selecting an individual suitable for treatment based on identifying whether that individual has a hemophilia disorder. In still other embodiments, the instructions comprise a description of administering a Kunitz polypeptide to an individual at risk of hemophilia.

The instructions relating to the use of a Kunitz polypeptide generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating or alleviating a hemophilic disorder. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a Kunitz polypeptide such as SEQ ID NO:1.

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Bioactivity of Kunitz Polypeptides

Materials

Lyophilized venom of *Daboia russelii russelii* (Pakistan) was purchased from Latoxan. Purified human activated protein C, protein S, factor XIIa (FXIIa), factor XIa (FXIa), factor Xa (FXa), factor IXa (FIXa), factor VIIa (FVIIa), factor Va (FVa), thrombin, plasma kallikrein and plasmin were obtained from Haematologic Technologies. Trypsin and tissue plasminogen activator (tPA) were from Merck Chemicals. Urokinase plasminogen activator (uPA) was a kind gift from Polyamine Corporation. Synthetic chromogenic substrates Spectrozyme PCa, Spectrozyme tPA and Spectrozyme FIXa were purchased from American Diagnostica, while S-2222, S-2302, S-2366, S-2288 and S-2251 were from Chromogenix. T-1637 was from Sigma-Aldrich. RVV-X was prepared from our laboratory according to the method provided by Chen et al[13]. Unfractionated heparin and heparan sulfate were from Sigma-Aldrich, while heparan sulfate (one, two, three or four disaccharide units long) were gifts from Dr. Hung Shang-Cheng (Genomics Research Center, Academia Sinica, Taiwan). Recombinant thrombomodulin (TM) was a gift from Dr. Wu Hua-Lin. Synthetic phospholipids 1,2-dioleoyl-sn-glycero-3-phosphocholine (DOPC), 1,2-dioleoyl-sn-glycero-3-phosphoethanolamine (DOPE) and 1,2-dioleoyl-sn-glycero-3-phosphoserine (DOPS) were bought from Avanti Polar Lipids. Normal coagulation control plasma, protein C-deficient plasma, FVIII-deficient plasma and FIX-deficient plasma were purchased from American Diagnostica. The CM5 sensor chip for surface plasmon resonance (SPR) analysis was purchased from GE Healthcare.

Methods (i) Purification of Kunitz-Type Protease Inhibitors

Lyophilized *Daboia russelii russelii* crude venom was dissolved in 0.1 M ammonium acetate (pH 6.5) and loaded onto a Superdex™ 75 10/300 GL column (GE Healthcare) connected to an AKTA FPLC system (GE Healthcare). The proteins were eluted at a flow rate of 1.0 ml/min and collected in volumes of 0.5 ml. The fractions were analyzed by SDS-PAGE, and those that contained proteins in the approximate range of 5 to 10 kDa were pooled together and lyophilized. The proteins were further purified by reversed-phase HPLC (Waters 600 HPLC pump and controller) on a Vydak C-18 (10 µm, 250×4.6 mm) column. Elution was carried out with a linear gradient of 20-50% acetonitrile in 0.07% w/w trifluoroacetic acid over a period of 60 minutes. The purity of each protein was assessed by SDS-PAGE and the protein concentrations determined by BCA Protein Assay Kit (Pierce Biotechnology). The molecular weights were determined by Q-TOF Ultima MALDI instrument (Micromass).

(ii) Cloning of Kunitz-Type Protease Inhibitors

*Daboia russelii formosensis* cDNAs prepared from the venom gland mRNA were amplified using the previously described specific primers for Kunitz-type protease inhibitors [14]. The sense primer was 5' CCAGACGGCTCCATCATG 3' (SEQ ID NO:12) while the antisense primer was 5' AAAAGGAATRATCCAGG 3'(SEQ ID NO 13). The conditions for PCR were as follows: denaturation at 92° C. for 1 minute, annealing at 60° C. for 1 minute, and extension at 72° C. for 1 minute (35 cycles). The PCR fragments were inserted into the pGEM-T easy vector (Promega Biotech) and transformed into JM109 *Escherichia coli* competent cells. The sequences of plasmid DNAs from the transformed colonies were obtained using the DNA-Sequencing System (Model 373A, PE-Applied Biosystems).

(iii) In Vitro Assays for the Inhibition of APC by DrKIn-I

All inhibition assays were performed in 96-wells microtiter plates in 25 mM Tris-HCl (pH 7.4), 150 mM NaCl, 2.5 mM $CaCl_2$ and 5 mg/ml BSA. For comparison between DrKIn-I and DrKIn-II, the amidolytic activity of 10 nM APC, with or without 0.1 U/ml heparin, was assayed in the presence or absence of equal molar concentrations of DrKIn-I or DrKIn-II. Immediately after the addition of APC, Spectrozyme PCa was added and the rates of p-nitroaniline release were monitored at 405 nm for 10 minutes at 37° C. For dose response curves, APC was mixed with different concentrations of DrKIn-I in the presence or absence of heparin. The final concentrations were as follows: APC (10 nM), heparin (0.1 U/ml) and DrKIn-I (0-100 nM in the presence of heparin and 0-12800 nM in the absence of heparin). Dose-response curves were fitted using GraphPad Prism (GraphPad Software). In other inhibition experiments, varying concentrations of heparin (0-1000 mil/nil) or different lengths of heparan sulfate chains (10 µg/ml) were added to equimolar concentrations of APC and DrKIn-I (20 nM each). In all the inhibition experiments, Spectrozyme PCa was added to a final concentration of 0.2 mM. Changes in absorbance were measured using SpectraMax $M2^e$ Microplate Reader (Molecular Devices).

In assays involving FVa, 20 nM purified FVa was incubated at 37° C. with a mixture containing 1 nM or 5 nM APC, 20 nM protein S, 20 µM DOPC/DOPS (75:25) and 5-250 nM DrKIn-I in the presence or absence of 0.1 U/ml heparin. At specific time intervals, 5 µl aliquots were removed and mixed with 50 µl of FV-deficient plasma. The residual FVa activities were quantified in a standard prothrombin time-based assay using a calibration curved obtained by adding variable amounts of FVa to FV-deficient plasma. All concentrations given were final concentrations.

(iv) Heparin Binding Assay

A 5 ml HiTrap Heparin HP column (GE Healthcare) that had been pre-equilibrated with 20 mM Tris-HCl buffer (pH 8.0) was loaded with 70 µg of DrKIn-I. After washing with 5 ml of equilibrating buffer, a 50 ml gradient from 0.0-1.0 M NaCl was applied at a flow rate of 5 ml/min and the salt concentration corresponding to the protein peak was determined as a measure of its heparin binding affinity.

(v) Surface Plasmon Resonance Analysis

Biacore T200 (GE Healthcare) was used for analysis. APC or PC dissolved in 10 mM acetate buffer (pH 5.0) was immobilized on a CM5 sensor chip to a response unit (RU) of 1000 with an amine coupling kit. Associations and dissociations of DrKIn-I were performed in 10 mM HEPES (N-2-hydroxyethylpiperazine-N'-2-ethanesulfonic acid; pH 7.4), 150 mM NaCl, 3 mM EDTA (ethylenediaminetetraacetic acid) and 0.05% P20 with a flow rate of 60 µl/min. The sensor surface was regenerated with 90 µl of 2 M $MgCl_2$ and the signals obtained were subtracted by that obtained from the reference channel that had not been coated with ligands. Binding kinetics were determined by global fitting to 1:1 Langmuir binding model using the Biaevaluation software (GE Healthcare).

(vi) Kinetic Analysis of APC Inhibition by DrKIn-I

APC was incubated with heparin and increasing concentrations of DrKIn-I for 3 minutes. The initial reaction velocities ($mOD_{405\,nm}$/min) were then determined at 37° C. after the addition of varying concentrations of Spectrozyme PCa. The final concentrations were as follows: APC (20 nM), heparin (0.1 U/ml), DrKIn-I (0-80 nM) and Spectrozyme PCa (0.025-0.4 mM). Initial velocities were plotted against inhibitor concentrations for each substrate concentration tested and the plots were subjected to nonlinear least squares regression using GraphPad Prism software. The inhibition constant ($K_i$) of DrKIn-I was determined by global fitting to Morrison's tight binding equation as shown below [15], $$V_s = (V_o/2E_t)\{[K_i' + I_t - E_t)^2 + 4K_i'E_t]^{1/2} - (K_i' + I_t - E_t)\} \quad \text{(Eq. 1)}$$

where $V_s$ is the steady state velocity in the presence of inhibitor, while $V_o$ is the velocity in the absence of inhibitor. $I_t$ is the total inhibitor concentration and $E_t$ is the total enzyme concentration. $K_i'$ is the apparent inhibition constant. For competitive inhibition, $K_i'$ is related to the true inhibition constant ($K_i$) by the following equation:

$$K_i' = K_i/(1 + S/K_m) \quad \text{(Eq. 2)}$$

where S is the substrate concentration and $K_m$ is the Michaelis-Menten constant for Spectrozyme PCa, which was determined to be 0.55 mM.

(vii) Selectivity Profile of DrKIn-I

DrKIn-I, with or without heparin, was screened for its inhibitory activity against trypsin and also against serine proteases in the coagulation cascade (FXIIa, FXIa, FXa, FIXa, FVIIa, thrombin and kallikrein) and in the fibrinolytic system (plasmin, tPA and uPA). The amidolytic activities of these proteases were determined in the presence or absence of equimolar concentrations of DrKIn-I using their respective chromogenic substrates.

(viii) APTT-Based APC Resistance Assay

50 µl of normal plasma, FVIII-deficient plasma or FIX-deficient plasma supplemented with 2 µg/ml heparan sulfate (four disaccharide units long) was exposed to APC (40 nM) and varying concentrations of DrKIn-I (50-200 nM). 50 µl of activated partial thromboplastin (APTT) reagent (HYPHEN Biomed) was added and incubated for 1 minute at 37° C. Finally, clotting was initiated by adding 50 µl of 20 mM $CaCl_2$. Coagulation times, which reflect the activities of APC, were recorded on a coagulometer (Hemostasis Analyzer KC-1; Sigma Diagnostics).

(ix) Thrombin Generation Assay

Briefly, 80 µl of either normal plasma, protein C-deficient plasma, FVIII-deficient plasma or FIX deficient plasma containing 2 µM corn trypsin inhibitor, 2 µg/ml heparan sulfate (four disaccharide units long), 30 µM DOPC/DOPS/DOPE (60:20:20) and 100 nM recombinant TM was incubated with 20 µl of 500-fold diluted TF solution (Innovin; Dade Behring) in the absence or presence of the indicated concentrations of DrKIn-I. Following incubation for 3 minutes at 37° C., thrombin generation was initiated by the dispensation of 20 µl of 2.5 mM fluorogenic substrate (Z-Gly-Gly-Arg-AMC.HCl) dissolved in 0.15 M NaCl, 60 mg/ml BSA and 100 mM $CaCl_2$. Measurements were taken at 1 minute intervals on a SpectraMax $M2^e$ Microplate Reader using an excitation wavelength of 360 nm and an emission wavelength of 460 nm. In some assays, experiments were performed in the absence of thrombomodulin. Results were evaluated using the Technothrombin TGA software (Technoclone).

Results (a) Purification and Cloning of Kunitz-Type Protease Inhibitors

In view of the fact that Kunitz-type protease inhibitors are relatively small with a length of only approximately 60 amino acids [16], the crude venom of *Daboia russelii russelii* was first separated into several fractions based on their molecular sizes by gel filtration. The fifth fraction (indicated by a horizontal bar in FIG. 1A) was then subjected to a second purification step using reversed-phase HPLC. The first two proteins that were eluted (designated DrKIn-I and DrKIn-II) had approximate yields of 1.7% (w/w) and 2.6% (w/w), respectively (FIG. 1B). The masses of these two proteins were determined by MALDI-TOF analysis, which gave an m/z signal of 7548.9 Da for DrKIn-I and an m/z signal of 6940.3 Da for DrKIn-II. The molecular weights of these two proteins were exactly identical to that of the two Kunitz-type protease inhibitors cloned from the venom gland of *Daboia russelii formosensis* (FIG. 1C) (accession numbers JN825729 and JN825730), confirming the identity of the first two proteins as Kunitz-type protease inhibitors. Exactly identical sequences have also been cloned from the venom gland of *Daboia russelii siamensis* (accession numbers A8Y7N4 and A8Y7N5), indicating that these Kunitz-type protease inhibitors may be conserved throughout the *Daboia russelii* species. Furthermore, the mass obtained for DrKIn-I and its inability to be sequenced by Edman degradation indicate that the N-terminal of DrKIn-I is in the form of a cyclic pyroglutamatic acid.

(b) DrKIn-I Inhibits APC in the Presence of Heparin

The ability of DrKIn-I and DrKIn-II to inhibit APC amidolytic activity was assayed with a chromogenic synthetic substrate, Spectrozyme PCa. As shown in FIG. 2A, both inhibitors exhibited little inhibitory activity against APC in the absence of heparin. However, in the presence of 0.1 U/ml heparin (180 U/mg), DrKIn-I decreased the activity of APC by 100%, while DrKIn-II decreased the activity by only ~20%. Of the two Kunitz-type protease inhibitors purified, only DrKIn-I showed a potent inhibitory activity against APC. Dose-response curve of DrKIn-I obtained in the presence of heparin showed that the increase in inhibition occurred over a very narrow range of DrKIn-I concentration, as denoted by a large Hill slope of −3.64±0.30 (FIG. 2B). This indicates that DrKIn-I is a tight binding inhibitor of APC in the presence of heparin where the $K_d$ is much lower than the enzyme concentration [17]. Furthermore, complete inhibition was achieved for equimolar concentrations of APC and DrKIn-I (FIG. 2B). In contrast, the dose-response curve obtained in the absence of heparin was less steep, with a Hill slope of −0.85±0.02 (FIG. 2B). The $IC_{50}$ values in the presence and absence of heparin were 3.5±0.2 nM and 88.9±1.0 nM, respectively.

In order to determine the concentration of heparin required for the potentiation of APC inhibition, the enzyme-inhibitor mixture was spiked with varying concentrations of heparin. 0.01 U/ml of heparin potentiated the inhibition by more than 70% (FIG. 2C), and at 0.1 U/ml, no APC activity was detectable, suggesting that only low concentrations of heparin are required for APC inhibition.

Apart from heparin, the ability of heparan sulfate to potentiate DrKIn-I-mediated APC inhibition was also examined. As shown in FIG. 2D, heparan sulfate can also act as a cofactor for APC inhibition. Furthermore, while heparan sulfate chains of one disaccharide unit and 2 disaccharide units enhanced the inhibition by only ~10% and ~25%, respectively, heparan sulfate chain of 3 disaccharide units enhanced the inhibition by ~80%, suggesting that heparan sulfate chains should be at least 3 disaccharide units long for sufficient potentiation of APC inhibition (FIG. 2D).

Figure 2:
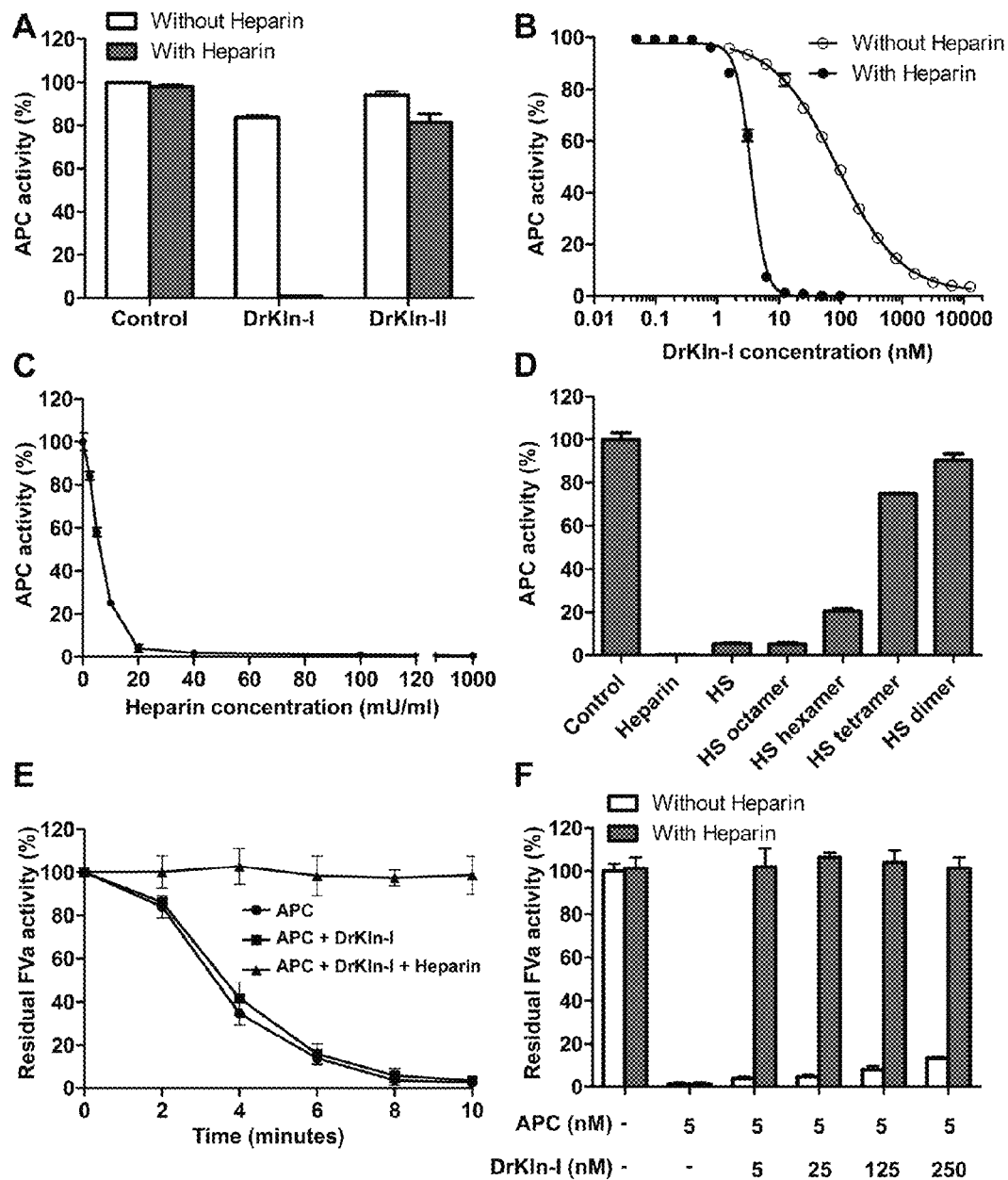
FIG. 2 shows inhibition of APC by DrKIn-I and DrKIn-II in the absence and presence of heparin. A: The ability of DrKIn-I and DrKIn-II (10 nM each) to inhibit the amidolytic activity of APC (10 nM) was compared using Spectrozyme PCa (0.2 mM) in the absence and presence of 0.1 U/ml heparin. B: Dose-response curves of APC (10 nM) inhibition by DrKIn-I in the absence (○) and presence (●) of 0.1 U/ml heparin. C: To determine the minimum concentration of heparin required for the potentiation APC inhibition, the activity of APC (20 nM) was measured after the addition of DrKIn-I (20 nM) and varying concentrations of heparin (0-1000 mU/ml). D: To assess the ability of heparan sulfate and the minimum length of heparan sulfate required to potentiate DrKIn-I-mediated APC inhibition, the amidolytic activity of APC was determined in the presence of DrKIn-I (20 nM) and different lengths of heparan sulfate chains (10 μg/ml each). E, Time course of FVa inactivation by APC (1 nM) was assessed in the absence (●) or presence (■) of 5 nM DrKIn-I, or in the presence of 5 nM DrKIn-I supplemented with 0.1 U/ml heparin (▲), as described in "Materials and methods". F, The effect of DrKIn-I (0-250 nM) and/or heparin (0.1 U/ml) on APC-mediated FVa inactivation was determined after 10 minutes of incubation at 37° C. with APC (5 nM). Results shown are means±SD of three experiments.

In addition to using the synthetic tripeptide (Spectrozyme PCa) as the substrate of APC, the inhibitory activity of DrKIn-I on FVa, which is APC's natural substrate, was tested. In the absence of heparin, APC (1 nM) progressively degraded FVa (20 nM) over a period of 10 minutes (FIG. 2E). The addition of DrKIn-I (5 nM) alone had relatively no effect on APC activity. However, in the presence of heparin, DrKIn-I (5 nM) protected 100% of FVa from inactivation (FIG. 2E). Without heparin, the addition of a 50-fold molar excess of DrKIn-I (250 nM) protected only less than 20% of FVa from inactivation (FIG. 2F), confirming that heparin is absolutely essential for DrKIn-I-mediated APC inhibition. Regardless of the type of substrate used, heparin alone at 0.1 U/ml did not alter the activity of APC (FIG. 2, A and F).

(c) Physical Interactions of DrKIn-I with Heparin and APC

Figure 3:
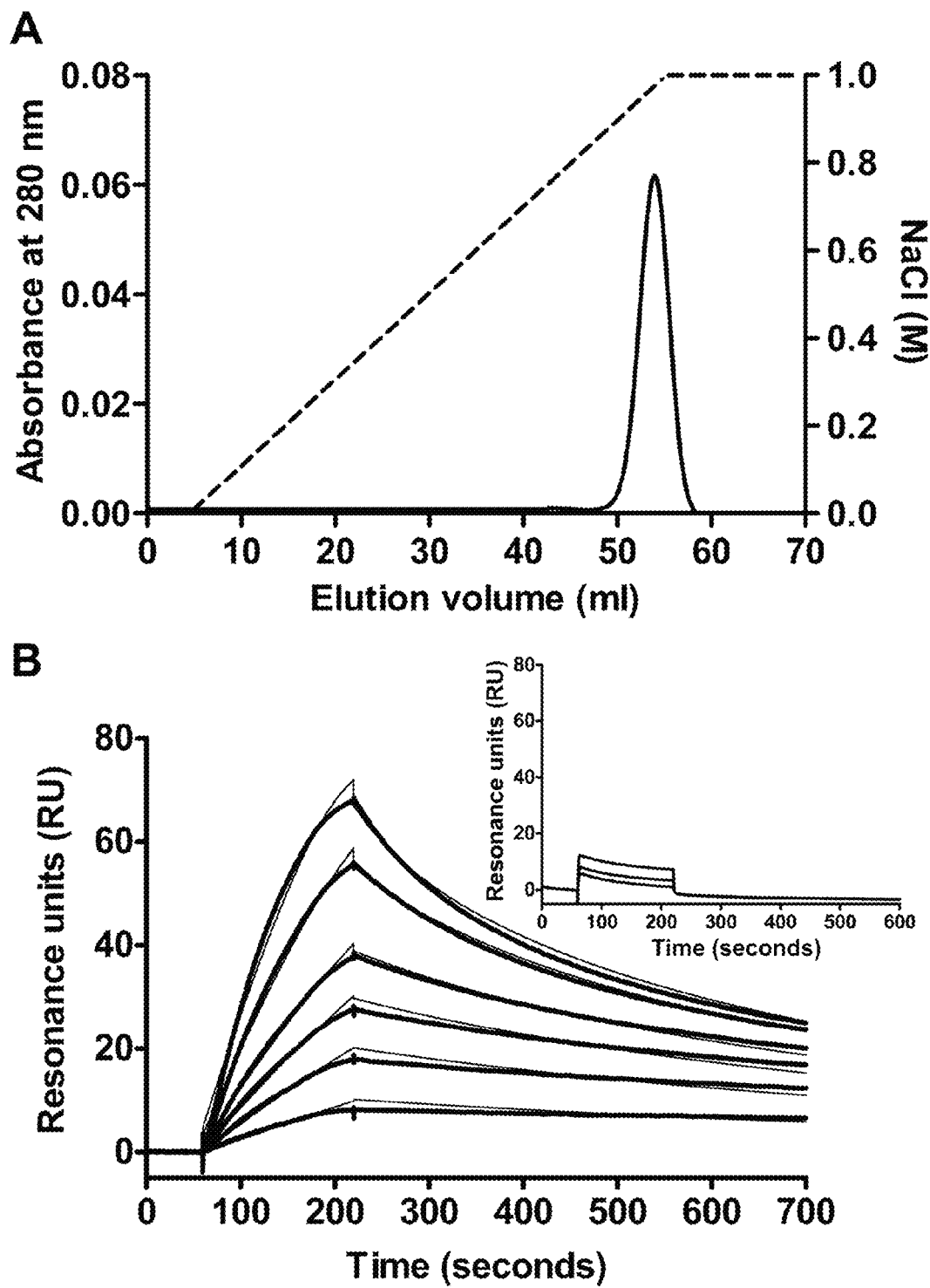
FIG. 3 shows physical interactions of DrKIn-I with heparin and APC. A: 70 μg of DrKIn-I in 0.1 ml equilibrating buffer (20 mM Tris-HCl, pH 8.0) was applied to a 5 ml HiTrap Heparin column and eluted with a 50 ml gradient from 0.0-1.0 M NaCl. The salt concentration corresponding to the elution peak was determined to be 0.95 M. B, Binding of DrKIn-I (0.78, 1.56, 2.34, 3.13, 4.68 and 6.25 nM) to immobilized APC was assessed in buffer containing 10 mM HEPES, 0.15 M NaCl, 3 mM EDTA and 0.05% P20 at a flow rate of 60 μl/min at 25° C. The association and dissociation rate constants, determined by global fitting to 1:1 Langmuir binding model, were $1.3\pm0.8\times10^7$ $M^{-1}$ $s^{-1}$ and $3.4\pm2.2\times10^{-2}$ $s^{-1}$, respectively. The thin lines represent the global fit to the response data. No binding was observed when DrKIn-I (31.25, 62.5, 125 nM) was flowed across immobilized PC (inset). Results shown are means±SD of three experiments. Representative binding traces are shown.

APC possesses a heparin-binding site that allows it to physically interact with heparin [18]. The binding of DrKIn-I with both heparin and APC was characterized. The binding of DrKIn-I to heparin was assessed using a heparin-Sepharose column. As expected, DrKIn-I bound to the heparin column with a very high affinity (FIG. 3A). The inhibitor eluted at 0.95 M NaCl, which was three times higher than that required for APC elution [19].

Next, the physical interactions between DrKIn-I and APC was investigated using surface plasmon resonance. DrKIn-I concentrations between 0.78 and 6.25 nM were flowed across an APC-coated CM5 sensor chip. DrKIn-I bound to immobilized APC with a $K_d$ of ~2.6±2.3 nM (FIG. 3B). The association rate constant was determined to be $1.3\pm0.8\times10^7$ $M^{-1}$ $s^{-1}$, which approached the diffusion limit of $10^6$~$10^8$ $M^{-1}$ $s^{-1}$ in aqueous solution [20, 21], while the dissociation rate constant was found to be $3.4\pm2.2\times10^{-2}$ $s^{-1}$. Interestingly, no binding was observed between DrKIn-I and the immobilized protein C zymogen (FIG. 3B inset).

(d) Determination of the Inhibition Constant of DrKIn-I

Figure 4:
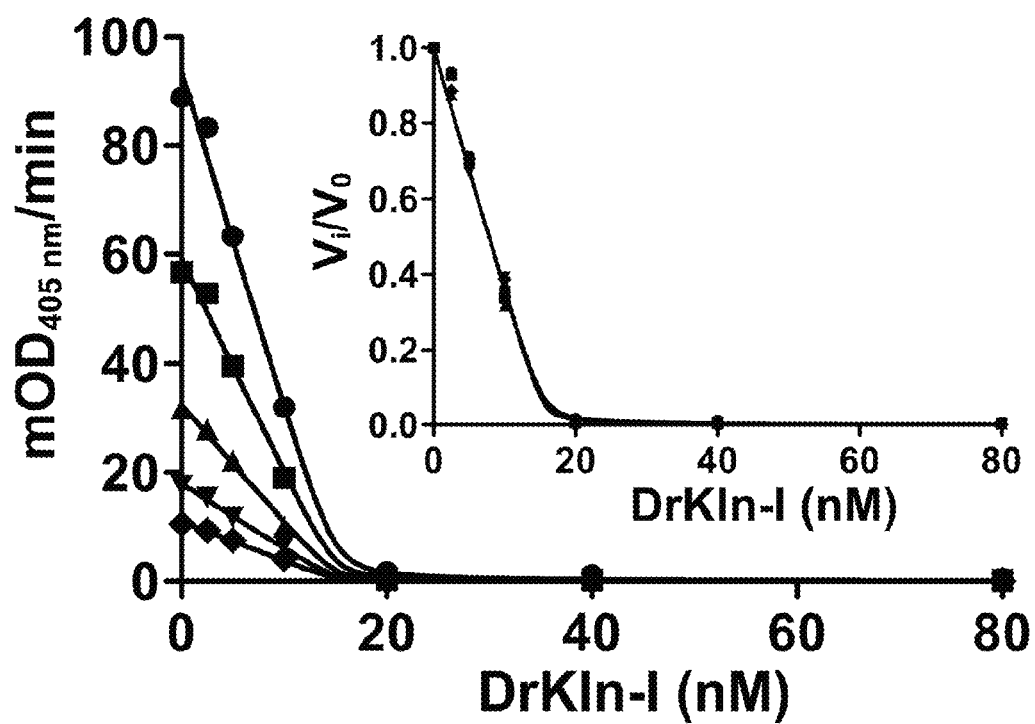
FIG. 4 shows kinetic analysis of APC inhibition by DrKIn-I in the presence of 0.1 U/ml heparin. Initial velocities of APC (20 nM) were measured in the presence of increasing concentrations of DrKIn-I (0-80 nM) using different concentrations of Spectrozyme PCa (●, 0.4 mM; ■, 0.2 mM; ▲, 0.1 mM; ▼, 0.05 mM; ♦, 0.025 mM) as substrate. Solid lines represent best least squares fit to Morrison's competitive tight binding equation, which gave an inhibition constant (Ki) of 53±39 pM. Inset shows the secondary plot of fractional velocity ($V_i/V_0$) versus DrKIn-I concentration, where Vi is the initial velocity in the presence of DrKIn-I and $V_0$ is the initial velocity in the absence of DrKIn-I.

Although DrKIn-I binds to APC in the absence of heparin, its effect on APC-mediated FVa degradation was negligible. The inhibition constant ($K_i$) of DrKIn-I was therefore determined only in the presence of heparin. By fitting the inhibition curves globally to Morrison's competitive tight binding equation, DrKIn-I was found to inhibit APC with a $K_i$ of 53±39 pM (FIG. 4). Although the plot of fractional velocity against inhibitor concentration showed overlapping inhibition curves for all the substrate concentrations tested (0.025-0.4 mM) (FIG. 4 inset), addition of a very high substrate concentration (3.3 mM) diminished the APC-inhibitory activity of DrKIn-I (data not shown), indicating that the inhibition is truly competitive in nature. The lack of substrate concentration effect therefore suggests that at lower substrate concentrations that are more experimentally feasible, the substrate is unable to effectively compete with the inhibitor.

(e) Selectivity Profile of DrKIn-I

Figure 5:
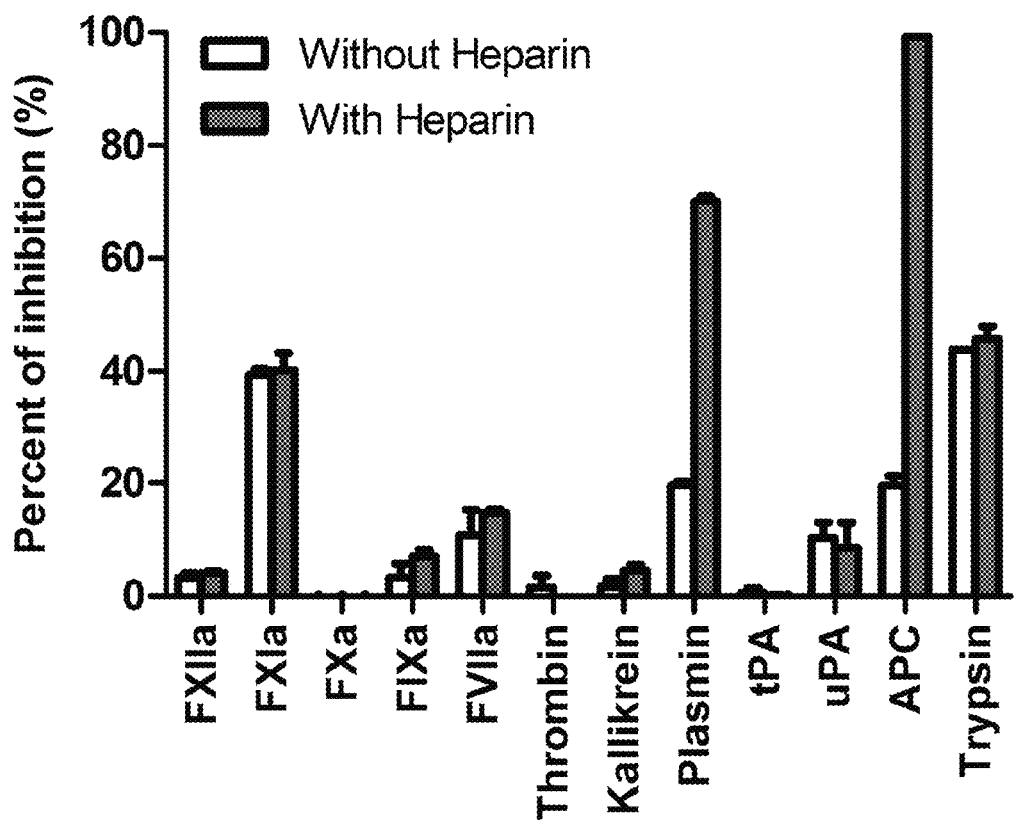
FIG. 5 shows selectivity profile of DrKIn-I. The inhibitory activity of DrKIn-I, in the presence or absence of heparin (0.1 U/ml), was screened against trypsin and also against serine proteases in the coagulation and fibrinolytic systems. In each of these experiments, the molar ratio of protease active site to inhibitor was 1:1. The final concentrations of these proteases and their respective substrates were as follows: FXIIa (20 nM)/S-2302 (0.2 mM), FXIa (2.5 nM)/S-2366 (0.2 mM), FXa (10 nM)/S-2222 (1.3 mM), FIXa (200 nM)/Spectrozyme FIXa (1.3 mM), FVIIa (100 nM)/S-2288 (1.3 mM), thrombin (5 nM)/T-1637 (0.2 mM), kallikrein (5 nM)/S-2302 (0.2 mM), plasmin (20 nM)/S-2251 (0.2 mM), tPA (80 nM)/Spectrozyme tPA (0.2 mM), uPA (100 nM)/S-2288 (1.3 mM), APC (10 nM)/Spectrozyme PCa (0.2 mM) and trypsin (5 nM)/S-2222 (0.2 mM). Results shown are means±SD of at least three experiments.

The inhibitory activity of DrKIn-I, in the presence or absence of heparin, was screened against the classic serine protease trypsin and also against serine proteases in the coagulation and fibrinolytic systems. Apart from APC, DrKIn-I at the same molar concentration as the enzyme active site also significantly inhibited the activities of trypsin (~45% inhibition), FXIa (~40% inhibition), and plasmin (~20% inhibition in the absence of heparin, and ~70% inhibition in the presence of heparin) (FIG. 5). Notably, among all the serine proteases tested, only APC showed 100% inhibition by DrKIn-I in the presence of heparin.

In order to compare the potencies of DrKIn-I against FXIa, plasmin and APC, the $K_i$ for FXIa and plasmin inhibition were also determined. Using chromogenic substrates, the $K_i$ values for FXIa and plasmin inhibition in the presence of heparin were found to be 1.33±0.08 nM and 1.56±0.09 nM, respectively (data not shown). These values were at least 25-fold higher than that for APC inhibition (~53 pM), supporting our hypothesis that APC is the preferential target of DrKIn-I.

(f) Inhibition of Endogenously Generated APC by DrKIn-I

Figure 6:
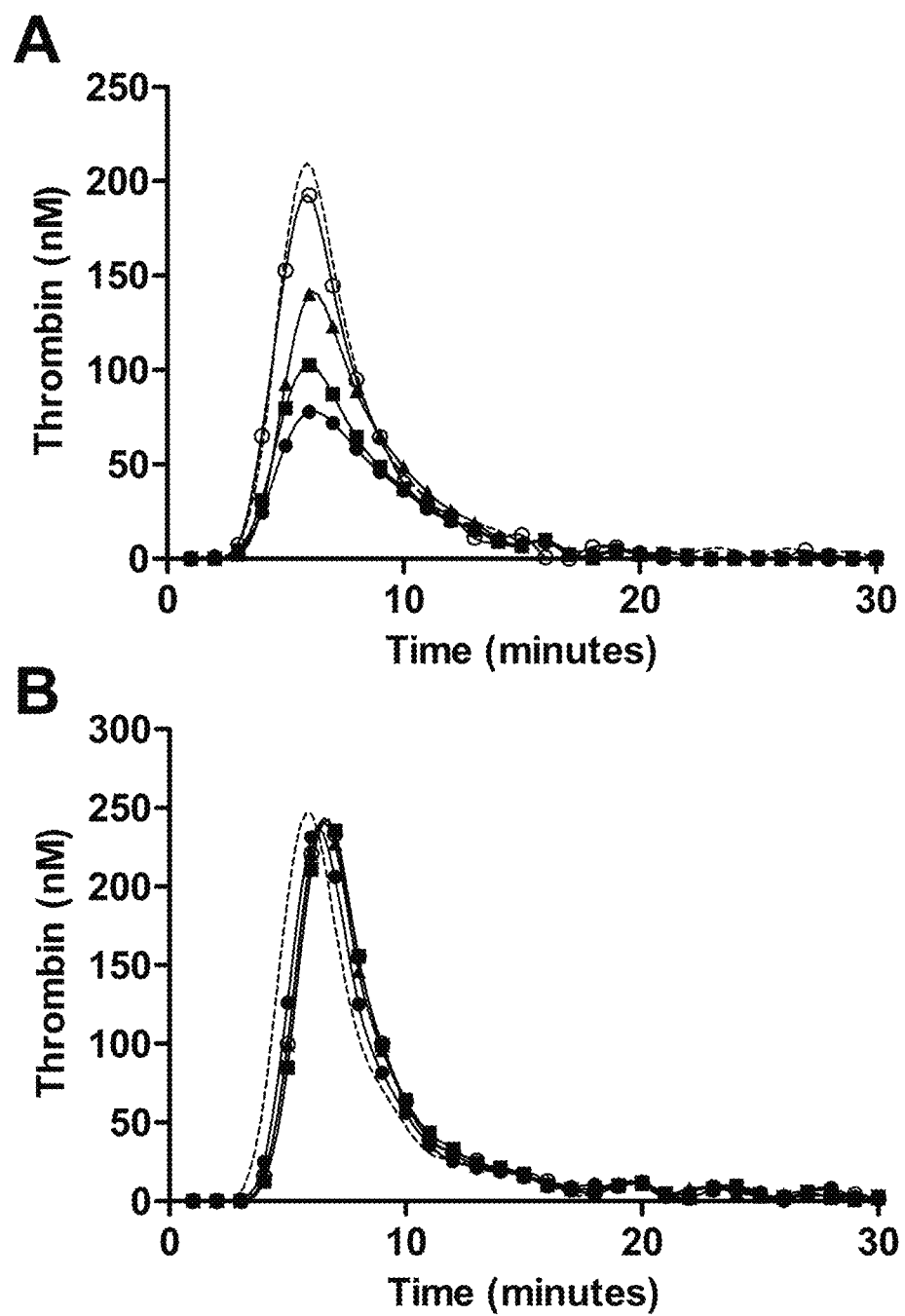
FIG. 6 shows the effect of DrKIn-I on thrombin generation in plasma. Thrombin generation in normal (A) and protein C-deficient (B) plasma. Experiments were performed in the presence of heparan sulfate (2 μg/ml). Solid lines represent thrombin generation in the presence of 100 nM thrombomodulin (TM) and varying concentrations of DrKIn-I (●, 0 nM; ■, 40 nM; ▲, 80 nM; ○, 200 nM). Dashed lines represent thrombin generation in the absence of TM and DrKIn-I.

Next, whether DrKIn-I inhibits the activity of endogenously generated APC in normal plasma was determined using the thrombin generation assay, which assesses the overall hemostatic state of the plasma. In the assay system described herein, the plasma was supplemented with TM, phospholipid vesicles and heparan sulfate before initiating the thrombin generation with TF so that the generated thrombin could form a complex with the added thrombomodulin and activate the endogenous protein C zymogen, while heparan sulfate acted as a cofactor for DrKIn-I-mediated APC inhibition. As shown in FIG. 6A, the addition of TM markedly decreased the generation of thrombin in normal plasma. Addition of increasing concentrations of DrKIn-I to TM-containing plasma increased the maximum thrombin concentration in a dose-dependent manner, and at a maximal concentration of 200 nM, thrombin generation reached that observed in the absence of APC activity. No changes in the initiation phase were observed, which is consistent with the previous findings [10, 22]. In protein C-deficient plasma, the addition of TM did not decrease the generation of thrombin (FIG. 6B). Furthermore, the addition of DrKIn-I did not alter the thrombin generation profile in TM-containing protein C-deficient plasma, indicating that DrKIn-I has no TM- or APC-independent effects on thrombin generation.

Figure 7:
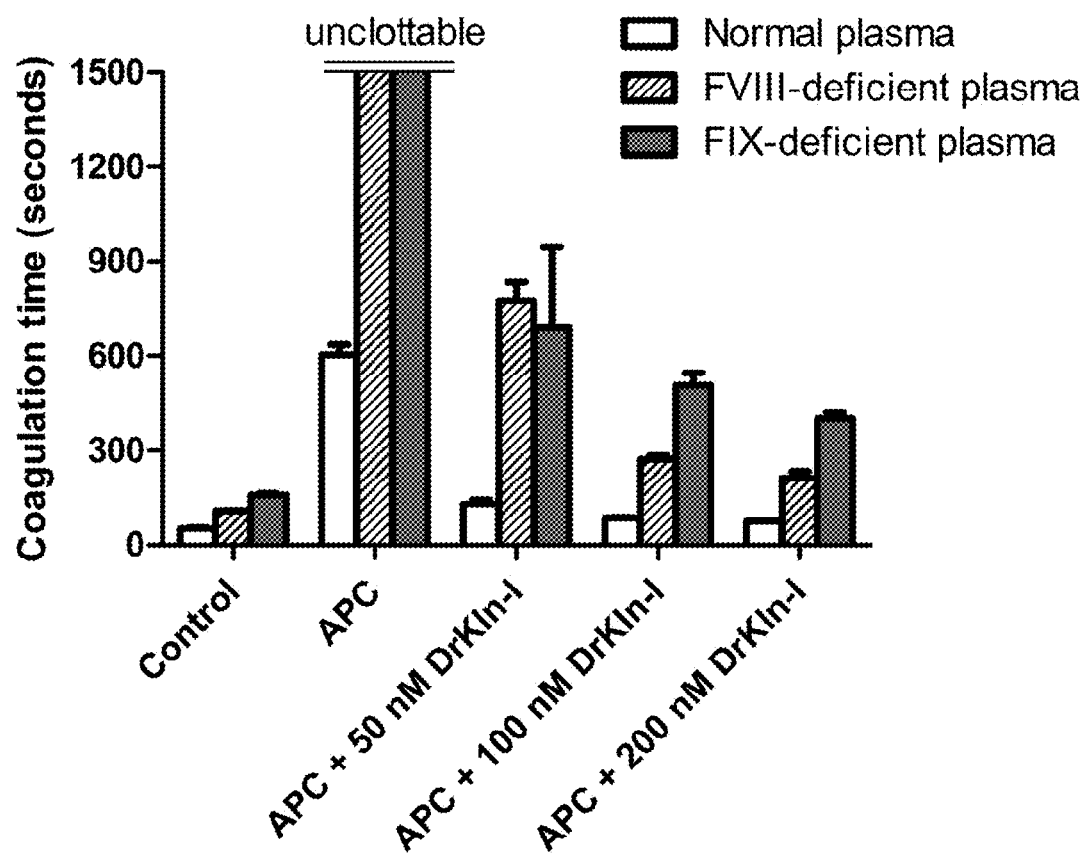
FIG. 7 shows DrKIn-I-mediated improvement of clotting times in normal, FVIII-deficient and FIX-deficient plasma. APTT-based clotting times were measured in normal, FVIII-deficient and FIX-deficient plasma containing 2 μg/ml heparan sulfate in the presence or absence of 40 nM APC and the indicated concentrations of DrKIn-I. Results shown are means±S.D. of at least three experiments.

(g) DrKIn-I Improves Clotting Times in Normal Plasma, FVIII-Deficient and FIX-Deficient Plasma The clotting abilities of normal plasma, FVIII-deficient plasma and FIX-deficient plasma in the presence of APC, heparan sulfate and varying concentrations of DrKIn-I were compared using the conventional APTT-based APC resistance assay. Interestingly, while the addition of 40 nM APC prolonged the clotting time of normal plasma to approximately 600 s, FVIII-deficient and FIX-deficient plasma failed to clot even after 1500 s, suggesting that APC may play an important role in preventing the hemostasis of hemophilic blood. As shown in FIG. 7, DrKIn-I dose-dependently decreased the clotting time for each of the APC-containing plasma. For normal and FVIII-deficient plasma, 200 nM DrKIn-I almost completely restored the clotting time to that observed in the absence of APC.

Figure 8:
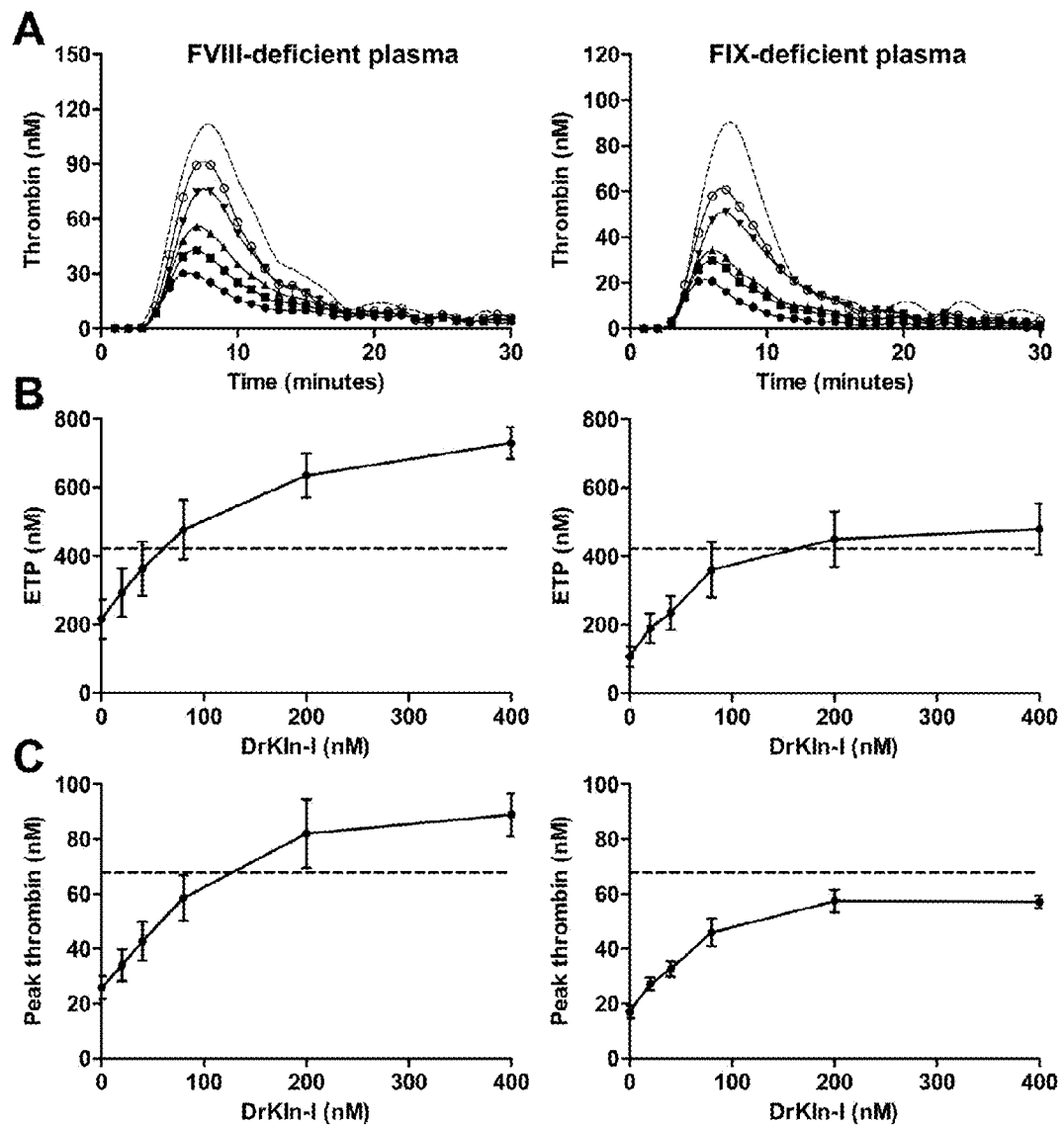
FIG. 8 shows the effect of DrKIn-I on thrombin generation in FVIII-deficient and FIX-deficient plasma. (A) Representative thrombin generation curves in FVIII-deficient and FIX-deficient plasma performed in the presence of heparan sulfate (2 μg/ml), TM (100 nM) and varying concentrations of DrKIn-I (●, 0 nM; ■, 20 nM; ▲, 40 nM; ▼, 80 nM; ○, 200 nM). Dashed lines represent thrombin generation in the absence of TM and DrKIn-I. (B-C) Activity in FVIII-deficient (B) and FIX-deficient (C) plasma. Left panels show ETP; right panels, peak thrombin. For comparison, dashed lines represent the activity of normal plasma containing TM and heparan sulfate in the absence of the inhibitor. Results are represented as means±SEM of at least three independent experiments.

(h) DrKIn-I Enhances Thrombin Generation in FVIII-Deficient and FIX-Deficient Plasma The ability of DrKIn-I to enhance thrombin generation was tested in FVIII-deficient or FIX-deficient plasma. As in previous thrombin generation assays, TM and heparan sulfate were added. The addition of TM significantly decreased the generation of thrombin in both FVIII-deficient and FIX-deficient plasma, which could be rescued by increasing concentrations of DrKIn-I (FIG. 8A). In order to quantify the therapeutic potential of DrKIn-I, two hemostatic parameters, namely endogenous thrombin potential (ETP; determined by the area under the thrombin generation curve) and peak thrombin level, for each concentration of DrKIn-I were obtained. In the absence of DrKIn-I, FVIII-deficient plasma exhibited an ETP of ~200 nM and a peak thrombin level of ~25 nM, values which were approximately 50% and 35% that of the normal plasma respectively (FIG. 8B). ETP was corrected to normal levels with 60 nM DrKIn-I, and peak thrombin was corrected with 130 nM DrKIn-I. FIX-deficient plasma had an even greater defect in thrombin generation, with an ETP of ~100 nM and a peak thrombin level of ~17 nM (FIG. 8C). Although the ETP could be corrected to normal levels with 160 nM of DrKIn-I, the peak thrombin level of FIX-deficient plasma was only partially corrected to approximately 85% that of the normal plasma. These results demonstrate that thrombin generation could be enhanced in FVIII- or FIX-deficient plasma using just nanomolar concentrations of DrKIn-I, making this unique inhibitor a plausible candidate for further studies in terms of hemophilia treatment.

Discussions

The data obtained from this study as discussed herein demonstrate that DrKIn-I is a potent, specific and heparin/heparan sulfate-dependent inhibitor of APC, and is able to compensate for the hemostatic defects in FVIII- or FIX-deficient plasma, as evidenced by both APTT-based clotting and thrombin generation assays. In the presence of DrKIn-I, the levels of thrombin generation triggered by TF in FVIII-deficient or FIX-deficient plasma approached, or in some cases exceeded, that in normal plasma.

In this study, FVIII-deficient (<1% FVIII) and FIX-deficient (<1% FIX) plasma were used as a model of severe hemophilia A and B, respectively, to analyze the therapeutic efficacy of DrKIn-I. The addition of TM and heparan sulfate chains to the thrombin generation assays reproduced the physiological conditions that occur in vivo, since both TM and heparan sulfate chains are abundant on the surface of endothelial cells [28, 29]. TM is particularly concentrated (~500 nM) in the microvasculature because the endothelial cell surface area per unit blood volume is much greater in the microcirculation than in other blood vessels. It is therefore suggested that small blood vessels could be better protected by DrKIn-I from hemorrhaging compared to larger blood vessels because it is assumed that the majority of protein C activation occurs in the microcirculation. This makes DrKIn-I particularly valuable because bleeding episodes in hemophilia typically originate from the microcirculation, such as the synovial capillary plexus [30].

Another advantage of DrKIn-I is the reduced risk of large vessel thrombosis because unlike other inhibitors that target tissue factor pathway inhibitor for hemophilia treatment [31, 32], DrKIn-I has no effect on thrombin generation when protein C is not activated.

The addition of APC to FVIII-deficient or FIX-deficient plasma dramatically prolonged the clotting time to the extent that the plasma became unclottable even after an hour. It is obvious from these APC resistance assays that the activation of the protein C pathway results in a secondary FVa deficiency, which further prevents the clotting of hemophilic blood. It is also evident from the thrombin generation data that APC alters only the propagation phase, and not the initiation phase of thrombin generation.

DrKIn-I is, by far, the most potent APC inhibitor found to date. It is a member of the snake Kunitz/BPTI family, and consists of 66 amino acids with three conserved disulfide linkages to stabilize the overall structure [16]. DrKIn-I is unique among all the other Kunitz-type protease inhibitors in that it is extremely basic (predicted pI=9.6), with two putative heparin-binding motifs in its C-terminal region ($^{49}$TRKKCRQ$^{55}$ and $^{60}$PRKGRP$^{65}$; SEQ ID NOs: 8 and 9) [34, 35]. The presence of these -$Z_1$BBB$Z_2$B$Z_3$- and -$Z_1$BB$Z_2$B$Z_3$- regions (where $Z_1$, $Z_2$, and $Z_3$ each represents uncharged amino acids and B represents basic amino acids) may contribute to the high affinity of DrKIn-I towards heparin/heparan sulfate and allows these oligosaccharides to potentiate the inhibition of APC by DrKIn-I. This is supported by the discoveries that although DrKIn-I and DrKIn-II are highly identical, with a percent identity of 71%, DrKIn-II, which lacks the heparin-binding motifs, showed no affinity towards heparin column (data not shown), and thus showed no inhibitory activity against APC.

Furthermore, the studies described herein show that DrKIn-I only requires a length of 3 disaccharide units to enhance the inhibition of APC by approximately 80%. This is in contrast with the typical template mechanism which requires heparin molecules to be at least 18 saccharide units long [37]. Since the association rate constant of DrKIn-I binding to APC is already diffusion limited in the absence of heparin/heparan sulfate (~1.3×10$^7$ M$^{-1}$ s$^{-1}$), the polysaccharide probably potentiates APC inhibition by forming a bridge between APC and DrKIn-I, locking them in the right orientation relative to each other and preventing them from dissociation.

Over the years, several plasma APC inhibitors belonging to the serpin family have been found, including protein C inhibitor and alpha-1-antitrypsin [38, 39]. In the absence of heparin, both serpins inhibit APC slowly, with second order rate constants of 2.5×10$^3$ M$^{-1}$ s$^{-1}$ and 1.0×10 M$^{-1}$ s$^{-1}$, respectively. DrKIn-I, however, is the first APC inhibitor discovered that belongs to the Kunitz/BPTI family. It differs from the serpin-type APC inhibitors in that it is not a slow-binding inhibitor. Using the synthetic substrate, DrKIn-I inhibited the amidolytic activity of APC as soon as it was added to the enzyme. While heparin enhances the second order rate constant of protein C inhibitor by 30- to 230-fold [38, 40], the binding between APC and DrKIn-I is intrinsically fast, with an association rate constant of ~1.3×10$^7$ M$^{-1}$ s$^{-1}$ These differences suggest that DrKIn-I is the only inhibitor discovered that exhibits fast-binding kinetics with APC.

The selectivity profile of DrKIn-I suggests that besides APC, the inhibitor may also target FXIa and plasmin. However kinetic analyses indicate that the $K_i$ for APC inhibition is at least 25-fold lower than that for FXIa and plasmin inhibition. The thrombin generation experiments with protein C-deficient plasma described herein also showed negligible effects of DrKIn-I on APC-independent thrombin generation. Furthermore, euglobulin clot lysis assays were performed on both DrKIn-I and aprotinin (a well known plasmin inhibitor) [41] in order to assess the plasmin inhibitory activity of DrKIn-I. Whereas 20 nM of aprotinin prolonged the euglobulin clot lysis time by ~9 hours, 20 nM of DrKIn-I failed to prolong the clot lysis time, either in the presence or absence of heparin. At a concentration of 100 nM, aprotinin prolonged the clot lysis time by more than 16 hours, while DrKIn-I only prolonged the clot lysis time by approximately an hour.

In summary, the present study demonstrates that DrKIn-I is a potent and specific inhibitor of APC and that it has the therapeutic potential for hemophilia treatment as judged by its ability to enhance thrombin generation in FVIII-deficient and FIX-deficient plasma. The fact that hemophilia patients often bleed from the microcirculation suggests that DrKIn-I may be used to protect the patients from microvascular bleedings without the risks of thrombosis in larger vessels.

Example 2

Heparin/Heparan Sulfate Binding Motifs in DrKIn-I Contribute to APC Inhibition

Figure 9:
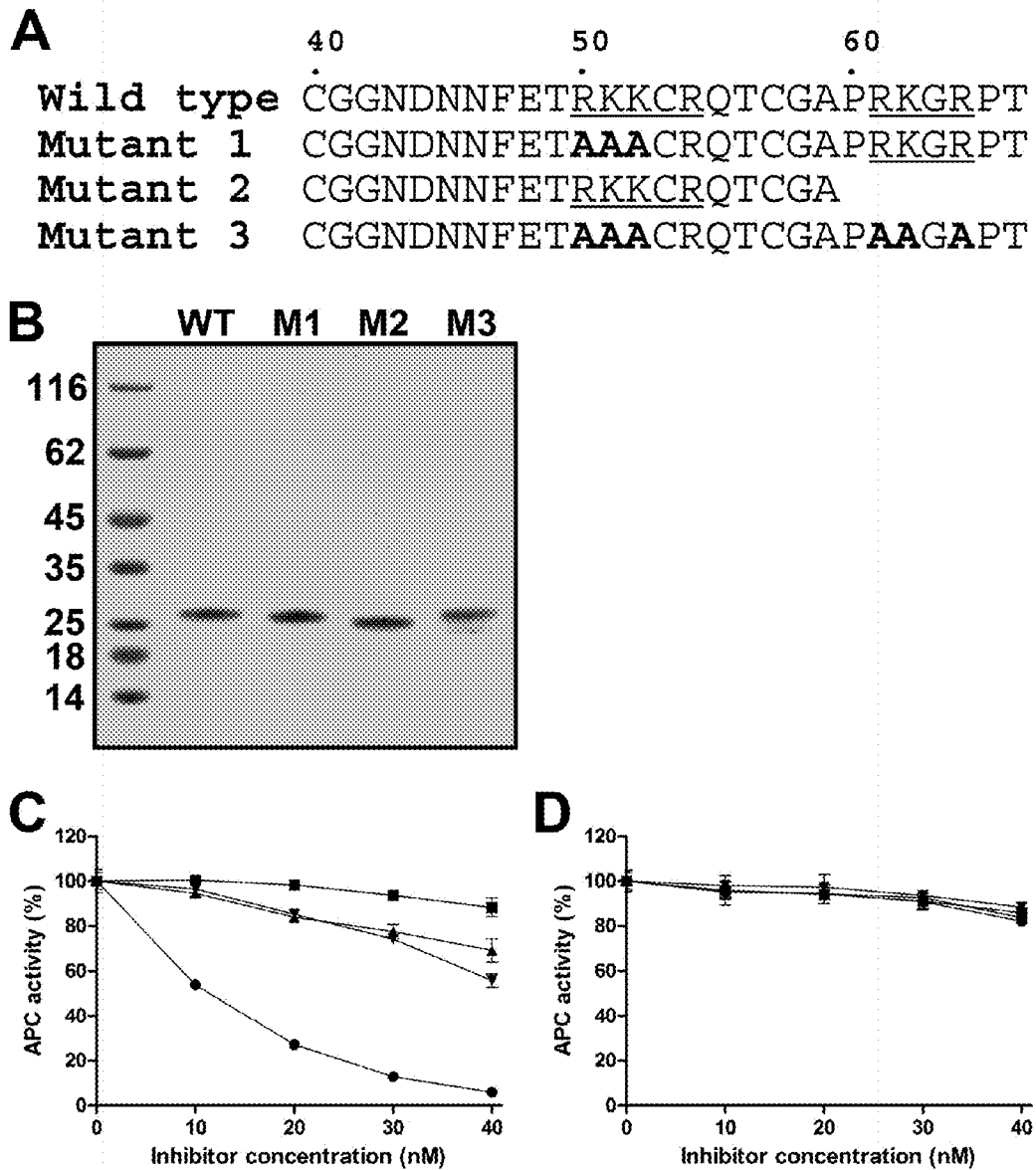
FIG. 9 shows the generation of DrKIn-I wild type and mutants. A: amino acid alignment of the C-terminal regions of the wild-type DrKIn-I peptide and three mutants, which were generated by either deleting or mutating (alanine substitution; denoted by bold letters) one or both of the C-terminus heparin binding motifs. Underlined amino acids are the putative heparin binding motifs. B: SDS-PAGE analysis of the wild-type and mutant DrKIn-I peptides. Wild-type: SEQ ID NO:3. Mutant 1: SEQ ID NO:4. Mutant 2: SEQ ID NO:5. Mutant 3: SEQ ID NO:6. C-D: Inhibitory effect of DrKIn-I wild type (●), mutant 1 (▲), mutant 2 (▼) and mutant 3 (■) on APC (20 nM) in the presence (C) or absence (D) of heparan sulfate (10 µg/ml). Activity of APC without the addition of inhibitors was considered as 100%.

To investigate the roles of the two putative heparin/heparan sulfate binding sites at the C-terminus of DrKIn-I ($^{49}$TRKKCRQ$^{55}$ and $^{60}$PRKGRP$^{65}$; SEQ ID NOs: 8 and 9) in APC inhibition, recombinant DrKIn-I mutants were generated in which the heparin/heparan sulfate binding sites were either deleted or substituted with alanines. Mutant 1 (KIn-R50A/K51A/K52A) and Mutant 2 (KIn-Δ60-66) lacked only one of the two heparin binding sites, while Mutant 3 (KIn-R50A/K51A/K52A/R61A/K62A/R64A) lacked both of the binding sites (FIG. 9A). Recombinant wild type DrKIn-I and mutants were prepared via the conventional recombinant technology (HIS-SUMO tagged) and the proteins thus obtained were examined by SDS-PAGE. Each His-SUMO tagged recombinant protein was purified to at least 90% purity and shown as a single major band on SDS-PAGE (FIG. 9B).

The wild-type DrKIn-I and the mutants at various concentrations were mixed with APC (20 nM) in the presence of heparin or heparan sulfate (10 μg/ml). After 3 minutes of incubation, a chromogenic substrate S-2366 (0.4 mM) was added and the rate of p-nitroaniline release was monitored at 405 nm for 10 minutes at 37° C. As shown in FIG. 9C, removal of either of the heparin/heparan sulfate-binding sites significantly inhibited the ability of heparan sulfate to potentiate APC inhibition, and removal of both the binding sites completely abrogated the potentiating effect of the polysaccharide. All of the recombinants displayed no differences in APC inhibition in the absence of heparan sulfate (FIG. 9D). On the other hand, Mutants 1 and 2 inhibit APC in the presence of heparin. These results indicate that the heparin/heparan sulfate binding motifs of DrKIn-I ($^{49}$TRKKCRQ$^{55}$ and/or $^{60}$PRKGRP$^{65}$; SEQ ID NOs: 8 and 9) are important for efficient APC inhibition in the presence of heparan sulfate.

REFERENCES

1 Bolton-Maggs P H, Pasi K J. Haemophilias A and B. *Lancet.* 2003; 361: 1801-9.
2 Srivastava A, Brewer A K, Mauser-Bunschoten E P, Key N S, Kitchen S, Llinas A, Ludlam C A, Mahlangu J N, Mulder K, Poon M C, Street A. Guidelines for the management of hemophilia. *Haemophilia.* 2012: 1-47.
3 Nichols W C, Amano K, Cacheris P M, Figueiredo M S, Michaelides K, Schwaab R, Hoyer L, Kaufman R J, Ginsburg D. Moderation of hemophilia A phenotype by the factor V R506Q mutation. *Blood.* 1996; 88: 1183-7.
4 Lee D H, Walker I R, Teitel J, Poon M C, Ritchie B, Akabutu J, Sinclair G D, Pai M, Wu J W, Reddy S, Carter C, Growe G, Lillicrap D, Lam M, Blajchman M A. Effect of the factor V Leiden mutation on the clinical expression of severe hemophilia A. *Thromb Haemost.* 2000; 83: 387-91.
5 Vianello F, Belvini D, Dal Bello F, Tagariello G, Zanon E, Lombardi A M, Zerbinati P, Girolami A. Mild bleeding diathesis in a boy with combined severe haemophilia B (C(10400)→T) and heterozygous factor V Leiden. *Haemophilia.* 2001; 7: 511-4.
6 Escuriola Ettingshausen C, Halimeh S, Kurnik K, Schobess R, Wermes C, Junker R, Kreuz W, Pollmann H, Nowak-Gottl U. Symptomatic onset of severe hemophilia A in childhood is dependent on the presence of prothrombotic risk factors. *Thromb Haemost.* 2001; 85: 218-20.
7 Franchini M, Lippi G. Factor V Leiden and hemophilia. *Thromb Res.* 125: 119-23.
8 Griffin J H, Fernandez J A, Gale A J, Mosnier L O. Activated protein C. *J Thromb Haemost.* 2007; 5 Suppl 1: 73-80.
9 Schlachterman A, Schuettrumpf J, Liu J H, Furlan Freguia C, Toso R, Poncz M, Camire R M, Arruda V R. Factor V Leiden improves in vivo hemostasis in murine hemophilia models. *J Thromb Haemost.* 2005; 3: 2730-7.
10 Brummel-Ziedins K E, Whelihan M F, Rivard G E, Butenas S. Activated protein C inhibitor for correction of thrombin generation in hemophilia A blood and plasmal. *J Thromb Haemost.* 9: 2262-7.
11 De Nanteuil G, Gloanec P, Beguin S, Giesen P L, Hemker H C, Mennecier P, Rupin A, Verbeuren T J. Low molecular weight activated protein C inhibitors as a potential treatment for hemophilic disorders. *J Med Chem.* 2006; 49: 5047-50.
12 Cheng A C, Wu H L, Shi G Y, Tsai I H. A novel heparin-dependent inhibitor of activated protein C that potentiates consumptive coagulopathy in Russell's viper envenomation. *J Biol Chem.* 287: 15739-48.
13 Chen H S, Chen J M, Lin C W, Khoo K H, Tsai I H. New insights into the functions and N-glycan structures of factor X activator from Russell's viper venom. *FEBS J.* 2008; 275: 3944-58.
14 Cheng Y C, Yan F J, Chang L S. Taiwan cobra chymotrypsin inhibitor: cloning, functional expression and gene organization. *Biochim Biophys Acta.* 2005; 1747: 213-20.
15 Copeland R A. Tight Binding Inhibitors. In: Copeland R A, ed. *Enzymes: A Practical Introduction to Structure, Mechanism, and Data Analysis,* 2nd edn. New York: John Wiley & Sons, Inc., 2000, 305-17.
16 Zupunski V, Kordis D, Gubensek F. Adaptive evolution in the snake venom Kunitz/BPTI protein family. *FEBS Lett.* 2003; 547: 131-6.
17 Shoichet B K. Interpreting steep dose-response curves in early inhibitor discovery. *J Med Chem.* 2006; 49: 7274-7.
18 Friedrich U, Blom A M, Dahlback B, Villoutreix B O. Structural and energetic characteristics of the heparin-binding site in antithrombotic protein C. *J Biol Chem.* 2001; 276: 24122-8.
19 Petaja J, Fernandez J A, Gruber A, Griffin J H. Anticoagulant synergism of heparin and activated protein C in vitro. Role of a novel anticoagulant mechanism of heparin, enhancement of inactivation of factor V by activated protein C. *J Clin Invest.* 1997; 99: 2655-63.
20 Northrup S H, Erickson H P. Kinetics of protein-protein association explained by Brownian dynamics computer simulation. *Proc Natl Acad Sci USA.* 1992; 89: 3338-42.
21 van Holde K E. A hypothesis concerning diffusion-limited protein-ligand interactions. *Biophys Chem.* 2002; 101-102: 249-54.
22 Butenas S, Orfeo T, Kalafatis M, Mann K G. Peptidomimetic inhibitors for activated protein C: implications for hemophilia management. *J Thromb Haemost.* 2006; 4: 2411-6.
23 Chang J, Weinman A F, Thompson A R. Factor V Arg/Gln306 has no dominant influence of the severity of hemophilia when inherited concurrently. *Thromb Haemost* 1995; 73: 1368.
24 Arbini A A, Mannucci P M, Bauer K A. Low prevalence of the factor V Leiden mutation among "severe" hemophiliacs with a "milder" bleeding diathesis. *Thromb Haemost.* 1995; 74: 1255-8.
25 van't Veer C, Golden N J, Kalafatis M, Simioni P, Bertina R M, Mann K G. An in vitro analysis of the combination of hemophilia A and factor V (LEIDEN). *Blood.* 1997; 90: 3067-72.
26 Nichols W C, Seligsohn U, Zivelin A, Terry V H, Arnold N D, Siemieniak D R, Kaufman R J, Ginsburg D. Linkage of combined factors V and VIII deficiency to chromosome 18q by homozygosity mapping. *J Clin Invest.* 1997; 99: 596-601.
27 Bos M H, Meijerman D W, van der Zwaan C, Mertens K. Does activated protein C-resistant factor V contribute to thrombin generation in hemophilic plasma? *J Thromb Haemost.* 2005; 3: 522-30.
28 Esmon C T. The roles of protein C and thrombomodulin in the regulation of blood coagulation. *J Biol Chem.* 1989; 264: 4743-6.
29 Ihrcke N S, Wrenshall L E, Lindman B J, Platt J L. Role of heparan sulfate in immune system-blood vessel interactions. *Immunol Today.* 1993; 14: 500-5.
30 Brown D L. Congenital bleeding disorders. *Curr Probl Pediatr Adolesc Health Care.* 2005; 35: 38-62.

31 Prasad S, Lillicrap D, Labelle A, Knappe S, Keller T, Burnett E, Powell S, Johnson K W. Efficacy and safety of a new-class hemostatic drug candidate, AV513, in dogs with hemophilia A. *Blood.* 2008; 111: 672-9.
32 Waters E K, Genga R M, Schwartz M C, Nelson J A, Schaub R G, Olson K A, Kurz J C, McGinness K E. Aptamer ARC19499 mediates a procoagulant hemostatic effect by inhibiting tissue factor pathway inhibitor. *Blood.* 117: 5514-22.
33 Stearns-Kurosawa D J, Kurosawa S, Mollica J S, Ferrell G L, Esmon C T. The endothelial cell protein C receptor augments protein C activation by the thrombin-thrombomodulin complex. *Proc Natl Acad Sci USA.* 1996; 93: 10212-6.
34 Cardin A D, Weintraub H J. Molecular modeling of protein-glycosaminoglycan interactions. *Arteriosclerosis.* 1989; 9: 21-32.
35 Fromm J R, Hileman R E, Caldwell E E, Weiler J M, Linhardt R J. Pattern and spacing of basic amino acids in heparin binding sites. *Arch Biochem Biophys.* 1997; 343: 92-100.
36 Griffith M J. Kinetics of the heparin-enhanced antithrombin III/thrombin reaction. Evidence for a template model for the mechanism of action of heparin. *J Biol Chem.* 1982; 257: 7360-5.
37 Hirsh J, Anand S S, Halperin J L, Fuster V. Mechanism of action and pharmacology of unfractionated heparin. *Arterioscler Thromb Vasc Biol.* 2001; 21: 1094-6.
38 Suzuki K, Nishioka J, Kusumoto H, Hashimoto S. Mechanism of inhibition of activated protein C by protein C inhibitor. *J Biochem.* 1984; 95: 187-95.
39 Heeb M J, Griffin J H. Physiologic inhibition of human activated protein C by alpha 1-antitrypsin. *J Biol Chem.* 1988; 263: 11613-6.
40 Espana F, Berrettini M, Griffin J H. Purification and characterization of plasma protein C inhibitor. *Thromb Res.* 1989; 55: 369-84.
41 Kang H M, Kalnoski M H, Frederick M, Chandler W L. The kinetics of plasmin inhibition by aprotinin in vivo. *Thromb Res.* 2005; 115: 327-40.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for inhibiting activated protein C (APC), comprising contacting the APC with a Kunitz polypeptide in an amount effective in inhibiting the activity of APC, wherein:
the Kunitz polypeptide comprises the amino acid sequence of SEQ ID NO:1.

2. The method of claim 1, wherein the contacting step is performed by administering to a subject in need thereof the Kunitz polypeptide.

3. The method of claim 2, wherein the subject is administered with the Kunitz polypeptide in an amount effective in promoting blood coagulation.

4. The method of claim 1, wherein the subject is a human patient suffering from or suspected of having a hemophilic disorder.

5. The method of claim 1, wherein the Kunitz polypeptide consists of the amino acid sequence of SEQ ID NO:1.

6. A method for treating a hemophilic disorder, comprising administering to a subject in need thereof an effective amount of a pharmaceutical composition comprising a pharmaceutically acceptable carrier and a Kunitz polypeptide, wherein:

the Kunitz polypeptide comprises the amino acid sequence of SEQ ID NO:1.

7. The method of claim 6, wherein the Kunitz polypeptide consists of the amino acid sequence of SEQ ID NO:1.

8. The method of claim 6, wherein the subject is a human patient having or suspected of having the hemophilic disorder.

* * * * *